US008101697B2

(12) United States Patent
Pawlow et al.

(10) Patent No.: US 8,101,697 B2
(45) Date of Patent: Jan. 24, 2012

(54) MULTI-FUNCTIONALIZED HIGH-TRANS ELASTOMERIC POLYMERS

(75) Inventors: James H. Pawlow, Akron, OH (US); Takayuki Yako, Kodaira (JP); Jason T. Poulton, Akron, OH (US); Sandra Warren, Massillon, OH (US); Christopher Robertson, Akron, OH (US)

(73) Assignee: Bridgestone Corporation, Tokyo (JP)

( * ) Notice: Subject to any disclaimer, the term of this patent is extended or adjusted under 35 U.S.C. 154(b) by 1565 days.

(21) Appl. No.: 11/344,660

(22) Filed: Feb. 1, 2006

(65) Prior Publication Data

US 2006/0173145 A1 Aug. 3, 2006

Related U.S. Application Data

(60) Provisional application No. 60/648,874, filed on Feb. 1, 2005, provisional application No. 60/649,419, filed on Feb. 2, 2005.

(51) Int. Cl.
*C08F 230/08* (2006.01)
*C08F 4/80* (2006.01)
*C08L 43/00* (2006.01)
*C07F 15/00* (2006.01)

(52) U.S. Cl. .......... 526/240; 526/75; 526/171; 526/279; 526/280; 526/281; 526/283; 526/308; 525/201; 525/209; 525/216

(58) Field of Classification Search ............... 526/75, 526/171, 240, 279, 281, 283, 308, 280; 525/201, 525/209, 216
See application file for complete search history.

(56) References Cited

U.S. PATENT DOCUMENTS

| | | | | |
|---|---|---|---|---|
| 3,816,382 A | 6/1974 | Streck et al. | | 260/93.1 |
| 3,816,384 A | 6/1974 | Streck et al. | | 260/677 |
| 3,857,825 A | 12/1974 | Streck et al. | | 260/88.1 |
| 3,920,714 A | 11/1975 | Streck | | 260/448 |
| 3,920,715 A | 11/1975 | Streck et al. | | 260/448 |
| 3,929,850 A | 12/1975 | Streck et al. | | 260/448 |
| 4,727,215 A | 2/1988 | Schrock | | 585/645 |
| 5,512,635 A * | 4/1996 | Nubel et al. | | 525/247 |
| 5,679,762 A | 10/1997 | Yoshida et al. | | 528/364 |
| 5,880,231 A | 3/1999 | Grubbs et al. | | |
| 6,300,451 B1 | 10/2001 | Mehta et al. | | 526/339 |
| 6,306,988 B1 * | 10/2001 | Grubbs et al. | | 526/172 |
| 6,465,590 B1 | 10/2002 | Maughon et al. | | |
| 6,593,005 B2 | 7/2003 | Tau et al. | | 428/516 |
| 6,605,748 B2 * | 8/2003 | Wagener et al. | | 568/852 |
| 6,624,265 B2 | 9/2003 | Grubbs et al. | | 526/135 |
| 6,777,490 B2 | 8/2004 | Mussig et al. | | 525/55 |
| 6,803,429 B2 | 10/2004 | Morgan et al. | | |
| 6,867,274 B2 | 3/2005 | Maughon et al. | | |
| 7,022,789 B2 | 4/2006 | Maughon et al. | | |
| 7,192,688 B2 * | 3/2007 | Klang et al. | | 430/270.1 |
| 2002/0137978 A1 * | 9/2002 | Grubbs et al. | | 585/507 |

OTHER PUBLICATIONS

Notestein, et al., Well-Defined Diblock Copolymers via Termination of Living ROMP with Anionically Polymerized Macromolecular Aldehydes, Macromolecules, vol. 35, No. 6, Mar. 12, 2002.*
Schapman, et al, "Low molar mass polybutadiene made crosslinkable by the introduction of silane moieties via urethane linkages . . . ," Polymer 39(4), 965-971 (1998).*
"Synthesis and Relaxation Dynamics of Multiarm Polybutadiene Melts" by Archer et al., Macromolecules, 31, pp. 6348-6355 (1998).
"Molecular Constitutive Equations for a Class of Branched Polymers: the Pom-Pom Polymer" by McLeish et al., Journal of Rheology, vol. 42, Issue 1 (Jan.-Feb. 1998) (Abstract).
"Evaluation of Rheological Constitutive Equation for Branched Polymers in Step Shear Strain Flow" by Schieber et al., Rheol Acta, vol. 42, pp. 123-131 (2003).
"Olefin Metathesis: Big-Deal Reaction" Rouhi, Chemical & Engineering News, vol. 80, No. 51 (Dec. 23, 2002).
"Ring Opending Metathesis Polymerization" Toreki, The Organometalli HyperTextBook (2003).
"Ab Initio Studies on Ruthenium-Based Olefin Metathesis Catalysts Mechanism" by Feldmann et al.
Utility of a Ruthenium Metathesis Catalyst for the Preparation of End-Functionalized—Marc A. Hillmyer, et al.—Macromolecules 1997, 30, 718-721.
Synthesis of Cross-Linkable Telechelic Poly(butenylene)s Derived from Ring-Opening Metathesis Polymerization—Bob R. Maughon, et al.—Macromolecules 2000, 33, 1929-1935.
A Ring-Opening Metathesis Polymerization (ROMP) Approach to Carboxyl- and Amino-Terminated Telechelic Poly(butadiene)s— Morita, et al.— Macromolecules 2000, 33, 6621-6623.
Highly efficient syntheses of acetoxy- and hydroxy-terminated telechelic poly(butadiene)s using ruthenium catalysts containing N-Heterocyclic ligands- Bielawski, et al., (2001).

* cited by examiner

*Primary Examiner* — Fred M Teskin
(74) *Attorney, Agent, or Firm* — Meredith E. Hooker; Arthur Reginelli

(57) ABSTRACT

A method for preparing multi-functional high-trans elastomeric polymers that have various applications such as in vulcanizable rubber compositions, moisture curable resin compositions, as well as other areas.

39 Claims, 1 Drawing Sheet

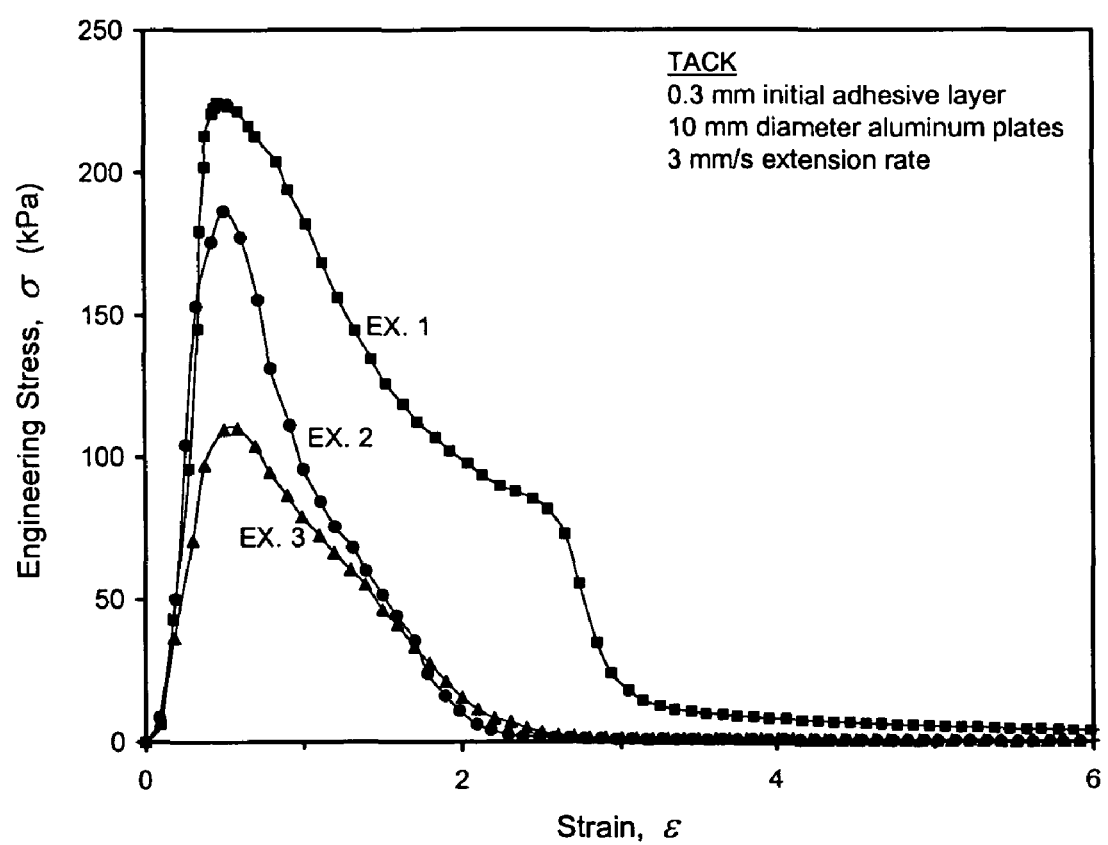

MULTI-FUNCTIONALIZED HIGH-TRANS ELASTOMERIC POLYMERS

This application claims the benefit of U.S. Provisional Application Nos. 60/648,874, filed Feb. 1, 2005, and 60/649,419, filed Feb. 2, 2005, which are incorporated herein by reference.

FIELD OF THE INVENTION

This invention relates to a method for preparing multi-functional elastomeric polymers.

BACKGROUND OF THE INVENTION

Moisture-curable adhesives and sealants are formulated to react with moisture to form a cured polymer layer with high strength and adhesive properties. Moisture is provided in the ambient air or may be adsorbed on the surface or absorbed within the porosity of many substrate materials.

Moisture-curable resins include cyanoacrylates, silicones, and polyurethanes. The cyanoacrylates operate as adhesives, and the silicone and polyurethane resins are used commonly as sealants, caulking, and gasketing, but they can also be employed as adhesives.

Silicone-type sealing materials typically include a polymer having a silicon-containing group that has a hydroxyl or hydrolyzable group bound to a silicon atom and can be crosslinked to form siloxane bonds. They have excellent weathering resistance and heat resistance.

Previous methods of preparing these sealing compositions include copolymerizing a crosslinkable silyl-containing (meth)acrylic monomer and another vinyl monomer. However in this method, silyl groups are randomly introduced into molecular chains, instead of at the ends of the chains. Also, a (meth)acrylic monomer has been polymerized in the presence of a crosslinkable silyl-containing mercaptan, a crosslinkable silyl-containing disulfide and a crosslinkable silyl-containing radical polymerization initiator. Acrylic monomer has been polymerized in the presence of a crosslinkable silyl-containing hydrosilane compound or a tetrahalosilane. It can be difficult by these methods, however, to introduce the crosslinkable group into the polymer at both termini with sureness. Thus, an insufficient gel fraction and insufficient curability results. Further, it can be difficult to control crosslinking density and to obtain a narrow molecular weight distribution. A method for preparing silicone-type moisture-curable sealant materials would be desirable.

Furthermore, the characteristics of the sealant compositions such as mechanical properties and viscosity upon melting depend upon the ratio between the number of block segments of the block copolymer and the molecular weight of the blocks. It would therefore be desirable to control the microstructure of the block copolymer.

In other areas, polymer molecules with long-chain side branches and more than one junction point have useful rheological properties. The idealized molecule, called a "pom-pom," has a single backbone, sometimes referred to as a crossbar, with multiple branches emerging from each end. The branches can become entangled with surrounding molecules, and the backbone can be stretched in an extensional flow, producing strain hardening. However, the shear rheology of these branched polymers can be shear thinning, as the backbone stretches only temporarily and eventually collapses as the molecule is aligned, producing strain softening.

The unique viscoelastic response of certain pom-pom polymer molecules in tension give them the ability to resist debondings and make them useful in adhesive applications. Branched polymers can also be used in elastomer formulations to improve green strength. Branched polymers can be prepared via anionic coupling reactions, but rigorous purification of solvents and monomers and careful fractionation of the polymer products is required. Also, when the methods are employed, it can be difficult to control and select the advantageous molecular weight of the branches and backbone for adhesive or elastomer applications.

SUMMARY OF THE INVENTION

One or more embodiments are directed toward a method for preparing a multi-functional alkene, the method comprising reacting at least two functional alpha olefin molecules in the presence of a metathesis catalyst to form an alkene comprising multiple functionalities.

Other embodiments are directed toward a method for preparing a multi-functional polymer, the method comprising the steps of reacting two or more alpha olefin molecules represented by the formula

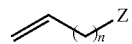

where each Z comprises a functional group and n is an integer from 0 to about 20.

Other embodiments are directed toward a method for preparing a multi-functional alkene, the method comprising reacting two or more alpha olefin molecules represented by the formula

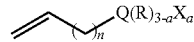

where Q comprises Si or Sn, each R independently comprises a hydroxyl, a hydrolyzable group, or a monovalent organic group containing from 1 to about 20 carbon atoms, each X comprises a hydrolyzable group or a hydroxyl group, a is an integer from 1 to about 3, and n is an integer from 0 to about 20, in the presence of a metathesis catalyst to form an alkene represented by the formula

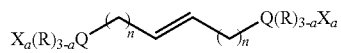

where each Q comprises Si or Sn, each R independently comprises a hydroxyl, a hydrolyzable group, or a monovalent organic group containing from 1 to about 20 carbon atoms, each X comprises a hydrolyzable group or a hydroxyl group, a is an integer from 1 to about 3, and n is an integer from 0 to about 20.

Other embodiments of the present invention are directed toward a method for preparing a multi-functional polymer, the method comprising reacting at least two functional alpha olefin molecules in the presence of a metathesis catalyst to form an alkene comprising multiple functionalities, where the alpha olefin molecules may be the same or different, and reacting the alkene with a cycloolefin in the presence of a ruthenium-based or osmium-based metathesis catalyst thereby forming a multi-functional polymer.

Other embodiments are directed toward a method for preparing a multi-functional polymer, the method comprising the step of reacting a cycloolefin, and an acyclic multifunctional alkene, in the presence of a ruthenium-based or osmium-based metathesis catalyst, where the multifunctional alkene comprises a tin-containing or silicon-containing group.

Still other embodiments are directed toward a method for preparing a multi-functional polymer comprising the steps of reacting two or more alpha olefin molecules represented by the formula

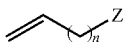

where each Z comprises a functional group and n is an integer from 0 to about 20 and where the alpha olefin molecules may be the same or different, in the presence of a metathesis catalyst thereby forming an alkene represented by the formula

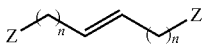

where each Z comprises a functional group and n is an integer from 0 to about 20, and reacting the alkene with a first cycloolefin and a second cycloolefin, in the presence of a metathesis catalysts (e.g., ruthenium-based or osmium-based metathesis catalyst) thereby forming a multi-functional polymer represented by the formula

where each Z comprises a functional group and $\sim\!\!\sim\!\!\sim$ comprises a polymer chain, and where the ratio of first cycloolefin to second cycloolefin is from about 99:1 to about 1:99.

Other embodiments are directed toward a method for preparing a multi-functional polymer, the method comprises reacting two or more alpha olefin molecules represented by the formula

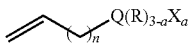

where Q comprises Si or Sn, each R independently comprises a hydroxyl, a hydrolyzable group, or a monovalent organic group containing from 1 to about 20 carbon atoms, each X comprises a hydrolyzable group or a hydroxyl group, a is an integer from 1 to about 3, and n is an integer from 0 to about 20, in the presence of a metathesis catalyst thereby forming an alkene represented by the formula

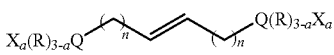

where each Q comprises Si or Sn, each R independently comprises a hydroxyl, a hydrolyzable group, or a monovalent organic group containing from 1 to about 20 carbon atoms, each X comprises a hydrolyzable group or a hydroxyl group, a is an integer from 1 to about 3, and n is an integer from 0 to about 20; and reacting the alkene with a first cycloolefin and a second cycloolefin, in the presence of a metathesis catalysts (e.g., a ruthenium-based or osmium-based metathesis catalyst) thereby forming a multi-functional polymer represented by the formula

where each Q comprises Si or Sn, each R independently comprises a hydroxyl, a hydrolyzable group, or a monovalent organic group containing from 1 to about 20 carbon atoms, each X comprises a hydrolyzable group or a hydroxyl group, and a is an integer from 1 to about 3, and $\sim\!\!\sim\!\!\sim$ comprises a polymer chain, and where the ratio of first cycloolefin to second cycloolefin is from about 99:1 to about 1:99.

Other embodiments are directed toward a method for preparing a multi-branched polymer, the method comprising (I) preparing a multifunctional polymer by reacting an olefin including a metathesis-active double bond and a compound represented by the formula

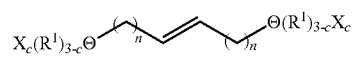

where each $\Theta$ independently includes carbon, silicon, germanium, tin, or lead, each $R^1$ independently includes hydrogen or a monovalent organic group, each X independently comprises a leaving group, each c independently includes an integer from 2 to 3, and each n is an integer from 0 to about 20 in the presence of a metathesis catalyst, and (II) combining the multifunctional polymer with living polymer to form the multi-branched polymer.

Yet other embodiments are directed toward a branched polymer that is represented by the formula

where each $\pi$ independently includes a polymer chain, $\sim\!\!\sim\!\!\sim$ comprises a polymer, each $\Theta$ independently includes carbon, silicon, germanium, tin, or lead, each $R^1$ independently includes hydrogen, or a monovalent organic group, and each c independently includes an integer from 2 to 3, where $\sim\!\!\sim\!\!\sim$ derives from a metathesis-catalyzed polymerization and each $\pi$ derives from an anionic polymerization.

Certain embodiments are directed toward a method for preparing a moisture-curable polymer, the method comprising the step of reacting (a) a first cycloolefin, (b) a second cycloolefin, where said second cycloolefin differs from said first cycloolefin in ring size or in substituents, or where said second cycloolefin is an isomer of said first cycloolefin, and (c) an acyclic alkene comprising at least one double bond and comprising multiple crosslinkable functional groups, in the presence of a ruthenium-based or osmium-based metathesis catalyst thereby forming a moisture-curable polymer, where the ratio of first cycloolefin to second cycloolefin is selected to produce a moisture-curable polymer having a melting point of from about minus 40 to about 50° C.

Other embodiments are directed toward a vulcanizable rubber composition comprising a multi-functional polymer prepared by reacting an alkene comprising multiple functionalities and a cycloolefin, in the presence of a ruthenium-based or osmium-based metathesis catalyst.

Other embodiments are directed toward a tire component prepared by a process comprising vulcanizing a rubber formulation that comprises a multi-functional polymer prepared by reacting an alkene comprising multiple functionalities and a cycloolefin, in the presence of a ruthenium-based or osmium-based metathesis catalyst.

BRIEF DESCRIPTION OF THE DRAWINGS

FIG. 1 is a plot of engineering stress versus strain for tack testing at 25° C.

DETAILED DESCRIPTION OF ILLUSTRATIVE EMBODIMENTS

In one or more embodiments, acyclic multi-functional alkenes can be prepared by reacting two or more functional alpha olefins in the presence of a metathesis catalyst. In certain embodiments, multi-functional polymers can be prepared by reacting the acyclic multi-functional alkene and a metathesis polymerizable olefin (e.g., cycloolefin) in the presence of a metathesis catalyst (e.g., ruthenium-based or osmium-based metathesis catalyst). In one or more embodiments, the multi-functional polymers include random copolymers and/or polymers having a high-trans microstructure. These polymers may include a wide variety of functional groups and may advantageously be telechelic (i.e., head- and tail-functionalized). In one embodiment, one or more multi-functional polymers are useful in moisture-curable sealant compositions. In other embodiments, one or more multi-functional polymers are useful in the preparation of rubber compositions such as those used in the manufacture of tires. In yet other embodiments, certain multi-functional polymers may be employed to prepare multi-branched polymers. These multi-branched polymers may be formed by reacting living polymer with certain multi-functional polymers.

Many metathesis catalysts are useful in practicing this invention. In one or more embodiments, the metathesis catalyst includes a transition metal carbene complex. Suitable transition metal carbene complexes include a positively charged metal center (e.g. in the +2, +4, or +6 oxidation state) that is penta- or hexa-coordinated. Exemplary transition metals include transition metals from Groups 3 to 12 of the Periodic Table, according to IUPAC conventions.

In one or more embodiments, the metathesis catalyst includes a ruthenium-based or osmium-based metathesis catalyst. Any ruthenium-based or osmium-based metathesis catalyst that is effective for ring-opening metathesis polymerization (ROMP) reactions can be used. Advantageously, certain ruthenium and/or osmium-based catalysts are unaffected or only immaterially affected by the presence of certain advantageous functional groups present on the alkene.

In one embodiment, the ruthenium-based or osmium-based metathesis catalysts includes carbene complexes of the type sometimes referred to as Grubbs catalysts. Grubbs metathesis catalysts are described in U.S. Pat. Nos. 5,312,940, 5,342,909, 5,831,108, 5,969,170, 6,111,121, 6,211,391, 6,624,265, 6,696,597 and U.S. Published App. Nos. 2003/0181609 A1, 2003/0236427 A1, and 2004/0097745 A9, all of which are incorporated herein by reference.

Ru- or Os-based metathesis catalysts include compounds that can be represented by the formula

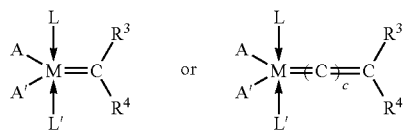 or 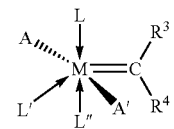

where M includes ruthenium or osmium, L and L' each independently include any neutral electron donor ligand, A and A' each independently include an anionic substituent, $R^3$ and $R^4$ independently comprise hydrogen or an organic group, and includes an integer from 0 to about 5, or where two or more of $R^3$, $R^4$, L, L', A, and A' combine to form a bidentate substituent.

In one embodiment, L and L' independently include phosphine, sulfonated phosphine, phosphite, phosphinite, phosphonite, arsine, stibnite, ether, amine, amide, imine, sulfoxide, carboxyl, nitrosyl, pyridine, thioether, trizolidene, or imidazolidene groups, or L and L' may together include a bidentate ligand. In one embodiment, L and/or L' include an imidizolidene group that can be represented by the formulas

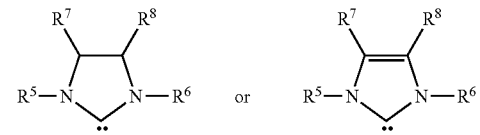

where $R^5$ and $R^6$ independently include alkyl, aryl, or substituted aryl. In one embodiment, $R^5$ and $R^6$ independently include substituted phenyls, and in another embodiment, $R^5$ and $R^6$ independently include mesityl. In one embodiment, $R^7$ and $R^8$ include alkyl or aryl, or form a cycloalkyl, and in another embodiment, are both hydrogen, t-butyl, or phenyl groups. Two or more of $R^5$, $R^6$, $R^7$ and $R^8$ can combine to form a cyclic moiety. Examples of imidazolidine ligands include 4,5-dihydro-imidazole-2-ylidene ligands.

In one embodiment, A and A' independently include halogen, hydrogen, $C_1$-$C_{20}$ alkyl, aryl, $C_1$-$C_{20}$ alkoxide, aryloxide, $C_2$-$C_{20}$ alkoxycarbonyl, arylcarboxylate, $C_1$-$C_{20}$ carboxylate, arylsulfonyl, $C_1$-$C_{20}$ alkylsulfonyl, $C_1$-$C_{20}$ alkylsulfinyl, each ligand optionally being substituted with $C_1$-$C_5$ alkyl, halogen, $C_1$-$C_5$ alkoxy, or with a phenyl group that is optionally substituted with halogen, $C_1$-$C_5$ alkyl, or $C_1$-$C_5$ alkoxy, and A and A' together may optionally include a bidentate ligand.

In one embodiment, $R^3$ and $R^4$ include groups independently selected from hydrogen, $C_1$-$C_{20}$ alkyl, aryl, $C_1$-$C_{20}$ carboxylate, $C_1$-$C_{20}$ alkoxy, aryloxy, $C_1$-$C_{20}$ alkoxycarbonyl, $C_1$-$C_{20}$ alkylthio, $C_1$-$C_{20}$ alkylsulfonyl and $C_1$-$C_{20}$ alkylsulfinyl, each of $R^3$ and $R^4$ optionally substituted with $C_1$-$C_5$ alkyl, halogen, $C_1$-$C_5$ alkoxy or with a phenyl group that is optionally substituted with halogen, $C_1$-$C_5$ alkyl, or $C_1$-$C_5$ alkoxy.

In one embodiment, L or L' and A or A' may combine to form one or more bidentate ligands. Examples of this type of complex are described as Class II catalysts in U.S. Pat. No. 6,696,597. In another embodiment, $R^3$ or $R^4$ and L or L' or A or A' may combine to form one or more bidentate ligands. This type of complex is sometimes referred to as Hoveyda or Hoveyda-Grubbs catalysts. Examples of bidentate ligands that can be formed by $R^3$ or $R^4$ and L or L' include ortho-alkoxyphenylmethylene ligands.

Other useful catalysts include hexavalent carbene compounds including those represented by the formula

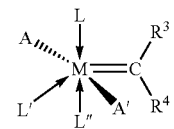

where M includes ruthenium or osmium, L, L', L" each independently include any neutral electron donor ligand, A, A', and A" each independently include an anionic substituent, and $R^3$ and $R^4$ independently comprise hydrogen or an organic group. In a manner similar to the penta-valent catalysts described above, one or more of the substituents in the hexa-valent complex may combine to form a bidentate substituent.

Examples of ruthenium-based carbene complexes include ruthenium, dichloro(phenylmethylene)bis(tricyclohexylphosphine), ruthenium, dichloro(phenylmethylene)bis(tricyclopentylphosphine), ruthenium, dichloro(3-methyl-2-butenylidene)bis(tricyclohexylphosphine), ruthenium, dichloro(3-methyl-2-butenylidene)bis(tricyclopentylphosphine), ruthenium, dichloro(3-phenyl-2-propenylidene)bis(tricyclohexylphosphine), ruthenium, dichloro(3-phenyl-2-propenylidene)bis (tricyclopentylphosphine), ruthenium, dichloro(ethoxymethylene)bis(tricyclohexylphosphine), ruthenium, dichloro(ethoxymethylene)bis(tricyclopentylphosphine), ruthenium, dichloro(t-butylvinylidene)bis (tricyclohexylphosphine), ruthenium, dichloro(t-butylvinylidene)bis(tricyclopentylphosphine), ruthenium, dichloro(phenylvinylidene)bis(tricyclohexylphosphine), ruthenium, dichloro(phenylvinylidene)bis(tricyclopentylphosphine), ruthenium, [2-(((2,6-bismethylethyl)-4-nitrophenyl)imino-kN)methyl-4-nitrophenolato-kO)]chloro-(phenylmethylene) (tricyclohexylphosphine), ruthenium, [2-(((2,6-bismethylethyl)-4-nitrophenyl)imino-kN)methyl-4-nitrophenolato-kO)]chloro-(phenylmethylene) (tricyclopentylphosphine), ruthenium, [2-(((2,6-bismethylethyl)-4-nitrophenyl)imino-kN)methyl-4-nitrophenolato-kO)]chloro-(3-methyl-2-butenylidene) (tricyclohexylphosphine), ruthenium[2-(((2,6-bismethylethyl)-4-nitrophenyl)imino-kN)methyl-4-nitrophenolato-kO)]chloro-(3-methyl-2-butenylidene) (tricyclopentylphosphine), ruthenium, [1,3-bis-(2,4,6-trimethylphenyl)-2-imidazolidinylidene][2-(((2,6-bismethylethyl)-4-nitrophenyl)imino-kN)methyl-4-nitrophenolato-kO)]chloro-(phenylmethylene), ruthenium, [1,3-bis-(2,4,6-trimethylphenyl)-2-imidazolidinylidene][2-(((2,6-bismethylethyl)-4-nitrophenyl)imino-kN)methyl-4-nitrophenolato-kO)]chloro-(3-methyl-2-butenylidene), ruthenium, dichloro[1,3-dihydro-1,3-bis-(2,4,6-trimethylphenyl)-2H-imidazol-2-ylidene](phenylmethylene) (tricyclohexylphosphine), ruthenium, dichloro[1,3-dihydro-1,3-bis-(2,4,6-trimethylphenyl)-2H-imidazol-2-ylidene](phenylmethylene)(tricyclopentylphosphine), ruthenium, dichloro[1,3-dihydro-1,3-bis-(2,4,6-trimethylphenyl)-2H-imidazol-2-ylidene](3-methyl-2-butenylidene)(tricyclohexylphosphine), ruthenium, dichloro[1,3-dihydro-1,3-bis-(2,4,6-trimethylphenyl)-2H-imidazol-2-ylidene](3-methyl-2-butenylidene) (tricyclopentylphosphine), ruthenium, dichloro[1,3-dihydro-1,3-bis-(2,4,6-trimethylphenyl)-2H-imidazol-2-ylidene](3-phenyl-2-propenylidene)(tricyclohexylphosphine), ruthenium, dichloro[1,3-dihydro-1,3-bis-(2,4,6-trimethylphenyl)-2H-imidazol-2-ylidene](3-phenyl-2-propenylidene) (tricyclopentylphosphine), ruthenium, dichloro[1,3-dihydro-1,3-bis-(2,4,6-trimethylphenyl)-2H-imidazol-2-ylidene](ethoxymethylene) (tricyclohexylphosphine), ruthenium, dichloro[1,3-dihydro-1,3-bis-(2,4,6-trimethylphenyl)-2H-imidazol-2-ylidene](ethoxymethylene) (tricyclopentylphosphine), ruthenium, dichloro[1,3-dihydro-1,3-bis-(2,4,6-trimethylphenyl)-2H-imidazol-2-ylidene](t-butylvinylidene) (tricyclohexylphosphine), ruthenium, dichloro[1,3-dihydro-1,3-bis-(2,4,6-trimethylphenyl)-2H-imidazol-2-ylidene](t-butylvinylidene)(tricyclopentylphosphine), ruthenium, dichloro[1,3-dihydro-1,3-bis-(2,4,6-trimethylphenyl)-2H-imidazol-2-ylidene](phenylvinylidene) (tricyclohexylphosphine), ruthenium, dichloro[1,3-dihydro-1,3-bis-(2,4,6-trimethylphenyl)-2H-imidazol-2-ylidene] (phenylvinylidene) (tricyclopentylphosphine), ruthenium, [1,3-bis-(2,4,6-trimethylphenyl)-2-imidazolidinylidene]-dichloro(phenylmethylene) (tricyclohexylphosphine), ruthenium, [1,3-bis-(2,4,6-trimethylphenyl)-2-imidazolidinylidene]-dichloro(phenylmethylene) (tricyclopentylphosphine), ruthenium, dichloro[1,3-bis-(2,4,6-trimethylphenyl)-2-imidazolidinylidene](3-methyl-2-butenylidene) (tricyclohexylphosphine), ruthenium, dichloro[1,3-bis-(2,4,6-trimethylphenyl)-2-imidazolidinylidene](3-methyl-2-butenylidene) (tricyclopentylphosphine), ruthenium, dichloro[1,3-bis-(2,4,6-trimethylphenyl)-2-imidazolidinylidene](3-phenyl-2-propylidene) (tricyclohexylphosphine), ruthenium, dichloro[1,3-bis-(2,4,6-trimethylphenyl)-2-imidazolidinylidene](3-phenyl-2-propylidene) (tricyclopentylphosphine), ruthenium, [1,3-bis-(2,4,6-trimethylphenyl)-2-imidazolidinylidene]-dichloro(ethoxymethylene) (tricyclohexylphosphine), ruthenium, [1,3-bis-(2,4,6-trimethylphenyl)-2-imidazolidinylidene]-dichloro(ethoxymethylene) (tricyclopentylphosphine), ruthenium, [1,3-bis-(2,4,6-trimethylphenyl)-2-imidazolidinylidene]-dichloro(t-butylvinylidene) (tricyclohexylphosphine), ruthenium, [1,3-bis-(2,4,6-trimethylphenyl)-2-imidazolidinylidene]-dichloro(t-butylvinylidene) (tricyclopentylphosphine), ruthenium, [1,3-bis-(2,4,6-trimethylphenyl)-2-imidazolidinylidene]-dichloro(phenylvinylidene) (tricyclohexylphosphine), and ruthenium, [1,3-bis-(2,4,6-trimethylphenyl)-2-imidazolidinylidene]-dichloro (phenylvinylidene) (tricyclopentylphosphine).

Commercially available Ru-based metathesis catalysts include ruthenium, dichloro(phenylmethylene)bis(tricyclohexylphosphine) (sometimes referred to as Grubbs First Generation Catalyst), ruthenium, [1,3-bis-(2,4,6-trimethylphenyl)-2-imidazolidinylidene]dichloro(phenylmethylene) (tricyclohexylphosphine) (sometimes referred to as Grubbs Second Generation Catalyst), ruthenium, dichloro[[2-(1-methylethoxy)phenyl]methylene](tricyclohexylphosphine), (sometimes referred to as Hoveyda-Grubbs First Generation Catalyst), and ruthenium, [1,3-bis(2,4,6-trimethylphenyl)-2-imidazolidinylidene]dichloro [[2, (1-methylethoxy)phenyl]methylene], (sometimes referred to as Hoveyda-Grubbs Second Generation Catalyst). These Ru-based metathesis catalysts are available from Materia Inc. (Pasadena, Calif.).

In one embodiment, the Ru-based or Os-based metathesis catalyst can be prepared in situ. For example, a Ru or Os compound can be combined with an alkyne and an appropriate ligand under known conditions to form a metal carbene complex such as those described above.

Other metathesis catalysts that are also useful include tungsten and/or molybdenum-based metathesis catalysts. These catalysts include those that may be formed in situ from salts such as tungsten salts, and molybdenum and tungsten complexes known as Schrock's carbenes. Tungsten-based metathesis catalysts are further described in U.S. Pat. Nos. 3,932,373, and 4,391,737, and Schrock catalysts are described in U.S. Pat. Nos. 4,681,956, 5,087,710, and 5,142,073, all of which are incorporated herein by reference.

In one or more embodiments, useful olefins include those that will undergo a metathesis reaction, i.e. those that include at least one metathesis-active double bond. The olefin may be cyclic or acyclic, and may include one or more substituent groups and/or functional groups. The cycloolefin may be a cycloalkene or a cyclopolyene. Oligomers of olefins are also useful.

In certain embodiments, the olefin includes a mixture of two or more different olefins that differ in at least one aspect including the number of carbon atoms or heteroatoms and the amount and kind of substituents. Two or more different olefins may also refer to two or more olefinic isomers. In one embodiment, the ratio of first olefin to second olefin is from about 99:1 to 1:99, in another embodiment from about 95:5 to 5:95, and yet another embodiment from about 90:10 to 10:90. The cycloolefin includes a mixture of two or more cycloolefins that differ in ring size or in substituents, or a mixture of two or more isomers of cycloolefins. Any combination of two or more cycloolefins can be used that provides the desired polymer properties, as discussed below. In one embodiment, the mixture includes 1,5-cyclooctadiene and cyclopentene.

As stated above, a multi-functional high-trans polymer can be prepared by reacting, in the presence of a metathesis catalyst, a cycloolefin, and a multifunctional alkene. Any cycloolefin that can participate in a ring-opening metathesis polymerization (ROMP) reaction may be used. The ring structure may be strained or unstrained. The cycloolefin may include one or more substituent groups and/or functional groups. The cycloolefin may be a cycloalkene or a cyclopolyene.

Cycloolefins include compounds represented by the formula

where z includes an integer from 1 to about 18. Examples of cycloolefins include cyclopropene, cyclobutene, benzocyclobutene, cyclopentene, dicyclopentadiene, norbornene, norbornadiene, cyclohexene, cycloheptene, cyclooctene, 7-oxanorbornene, 7-oxanorbornadiene, cyclodecene, 1,3-cyclooctadiene, 1,5-cyclooctadiene, 1,3-cycloheptadiene, [2.2.1]bicycloheptenes, bicyclooctenes, cyclohexenylnorbornenes, norbornene dicarboxylic anhydrides, cyclododecene, 1,5,9-cyclododecatriene, and derivatives thereof. It will be recognized by those of skill in the art that the thermodynamics of ring-opening polymerization varies based upon factors such as ring size and substituents. Ring-opening metathesis is described in K. J. Ivin and J. C. Mol, *Olefin Metathesis and Metathesis Polymerization*, Chap. 11 (1997), which is hereby incorporated by reference.

In one or more embodiments, the multi-functional alkene, which may also be referred to as a functionalizing agent, may include an acyclic functional alkene that includes at least one metathesis-active double bond. The acyclic multifunctional alkene may include an olefin having at least one metathesis active double bond and at least two functional end-groups. In one embodiment, the acyclic multifunctional alkene can be represented by the formula

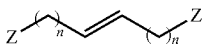

where each Z, which may be the same or different, includes a functional group and n includes an integer from 0 to about 20, in another embodiment, n includes an integer from about 1 to about 9, in yet another embodiment, n includes an integer less than about 6.

The functional group (Z) may include any group, moiety, or substituent that provides functionality to the polymer. In one or more embodiments, the functional group includes a hetero atom. In one or more embodiments, the functional group reacts or interacts with another constituent that the multi-functional polymer may be contacted with.

In certain embodiments, the functional group (Z) includes a crosslinkable moiety. Examples of crosslinkable functional groups include methacrylates, acrylates, cinnamates, epoxides, lactones, cyclic carbonates, tetrahydrofurans, oxetanes, lactams, phosphazenes, and tin- or silicon-containing groups that have a hydroxyl or hydrolyzable group bound to a tin or silicon atom. Hydrolyzable groups include hydrogen, halogen, alkoxy, acyloxy, ketoximate, amino, amide, aminoxy, mercapto, or alkenyloxy groups. Where two or more hydrolyzable groups or hydroxyl groups are present in the silicon-containing group, they may be the same or different.

In other embodiments, the functional group (Z) includes a filler interactive or reactive moiety. In other words, the functional group reacts or interacts with fillers such as carbon black or silica.

For example, functional groups that may react or interact with carbon black include polar groups, basic groups, and highly aromatic groups. Functional groups that may react or interact with silica include basic groups and groups capable of forming hydrogen bonds, such as hydroxyl, polyalkylene glycol, epoxy, alkoxy silane, and carboxylic acid groups. Exemplary functional groups include trialkyl tin substituents, primary, secondary, and tertiary amines, cyclic amine groups, silicon-containing groups such as alkoxy silyl groups, boron-containing compounds, isocyanatoalkoxysilane groups or sulfur-containing heterocycles. Other exemplary groups include substituents or residues of 1,3-dimethylimidazolidinone (DMI), N-methylpyrrolidinone (NMP), carbodiimides such as dicyclohexylcarbodiimide (DCC), benzonitrile or other substituted nitriles, substituted aziridines, thiazolines, dialkylaminobenzaldehydes, bis(dialkylamino)benzophenones, substituted epoxy compounds, N-methylcaprolactam, substituted Schiff bases, substituted styrylmethyl derivatives, vinyl pyridine, short blocks of polyvinylpyridine, polysulfoxides, poly(carbodiimides), poly(meth)acrylamides, poly(aminoalkyl(meth)acrylates), polyacrylonitrile, polyethylene oxide (PEO), butyl glycidyl ether, diphenyl ethylene, functionalized styrene, monoglycidyl siloxanes, and polysiloxanes having epoxide end groups. Examples of monoglycidyl siloxanes include 3-glycidoxypropyltrimethoxysilane (GP-MOS). Examples of polysiloxanes having epoxide end groups include monoglycidyl ether-terminated polysiloxanes such as monoglycidyl ether terminated poly(dimethylsiloxane).

Exemplary trialkyl tin substituents are disclosed in U.S. Pat. No. 5,268,439, which is incorporated herein by reference. Exemplary cyclic amine groups are disclosed in U.S. Pat. Nos. 6,080,853, 5,786,448, 6,025,450, and 6,046,288, which are incorporated herein by reference. Exemplary sulfur-containing heterocycles are disclosed in WO 2004/020475, which is incorporated herein by reference. Silicon-containing functional groups are disclosed in U.S. Pat. Nos. 6,008,295 and 6,228,908, which are incorporated herein by reference. Boron-containing functional groups are disclosed in U.S. Provisional Application No. 60/591,065, which is incorporated herein by reference. Exemplary isocyanatoalkoxysilane groups are disclosed in U.S. Provisional Application Ser. Nos. 60/477,012 and 60/477,013, which are incorporated herein by reference.

In one embodiment, the functional group (Z) can be represented by the formula

where Q includes Si or Sn, each R independently includes a hydroxyl, a hydrolyzable group, or a monovalent organic group containing from 1 to about 20 carbon atoms, each X includes a hydrolyzable group or a hydroxyl group, and a includes an integer from 1 to about 3. Monovalent organic groups include hydrocarbyl groups such as, but not limited to alkyl, cycloalkyl, substituted cycloalkyl, alkenyl, cycloalkenyl, substituted cycloalkenyl, aryl, allyl, substituted aryl, aralkyl, alkaryl, and alkynyl groups. In one embodiment, the monovalent organic group contains from 1 carbon atom, or the appropriate minimum number of carbon atoms to form the group, up to about 20 carbon atoms. These hydrocarbyl groups may contain heteroatoms such as, but not limited to, nitrogen, oxygen, silicon, sulfur, and phosphorus atoms.

Where Z comprises a silicon-containing crosslinkable functional group in one or more embodiments, the acyclic multi-functional alkene can be represented by the formula

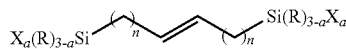

where each R, X, a, and n are as described above. Where Z comprises a tin-containing crosslinkable functional group, the acyclic multi-functional alkene can be represented by the formula

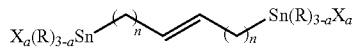

where each R, X, a, and n are as described above.

Examples of acyclic multifunctional alkenes include bis-silyl olefins, bis alkoxysilyl olefins, and bis halosilyl olefins, and tin analogs such as bis halostannyl olefins, bis alkoxystannyl olefins, and bis stannyl olefins. Bis silyl olefins and bis stannyl olefins include α,ω-bis(silyl)-alkenes, and α,ω-bis(stannyl)-alkenes, where the alkene portion includes from 2 to about 20 carbon atoms.

Bis halosilyl olefins include α,ω-bis(trihalosilyl)-, α,ω-bis(dihaloalkylsilyl)-, and α,ω-bis(halodialkylsilyl)-alkenes, where each halogen is independently fluorine, chlorine, bromine or iodine, each alkyl group is independently a $C_1$-$C_{20}$ alkyl, and the alkene portion includes from 4 to about 20 carbon atoms. Bis halostannyl olefins include α,ω-bis(trihalostannyl)-, α,ω-bis(dihaloalkylstannyl)-, and α,ω-bis(halodialkylstannyl)-alkenes, where each halogen is independently fluorine, chlorine, bromine or iodine, each alkyl group is independently a $C_1$-$C_{20}$ alkyl, and the alkene portion includes from 2 to about 20 carbon atoms.

Bis alkoxysilyl olefins include α,ω)-bis(trialkoxysilyl)-, α,ω)-bis(dialkoxyalkylsilyl)-, α,ω-bis(alkoxydialkylsilyl)-, α,ω-bis(halodialkoxysilyl)-, α,ω-bis(dihaloalkoxysilyl)-, and α,ω-bis(haloalkoxyalkylsilyl)-alkenes where each alkoxy group independently includes a $C_1$-$C_{10}$ alkoxy group, each halogen independently includes fluorine, chlorine, bromine, or iodine, each alkyl independently includes an alkyl having from 1 to about 20 carbon atoms, and the alkene portion includes from 2 to about 20 carbon atoms.

Examples of bis halosilyl olefins include 1,4-bis(trichlorosilyl)-butene, 1,4-bis(dichloromethylsilyl)-butene, 1,4-bis(chlorodimethylsilyl)-butene, 1,4-bis (dichloroethylsilyl)-butene, 1,4-bis(chlorodiethylsilyl)-butene, 1,4-bis(dichloropropylsilyl)-butene, 1,4-bis(chlorodipropylsilyl)-butene, 1,4-bis(dichlorobutylsilyl)-butene, 1,4-bis(chlorodibutylsilyl)-butene, and the fluoro, bromo and iodo analogs, the $C_5$-$C_{20}$ alkyl analogs, the mixed halo and mixed alkyl analogs, and the $C_5$-$C_{20}$ alkene analogs thereof.

Examples of bis alkoxysilyl olefins include 1,4-bis(trimethoxysilyl)-2-butene, 1,4-bis(dimethoxyalkylsilyl)-2-butene, 1,4-bis(methoxydialkylsilyl)-2-butene, 1,4-bis(chlorodimethoxysilyl)-2-butene, 1,4-bis(dichloromethoxysilyl)-2-butene, 1,4-bis(chloromethoxyalkylsilyl)-2-butene, 1,4-bis(triethoxysilyl)-2-butene, 1,4-bis(diethoxyalkylsilyl)-2-butene, 1,4-bis(ethoxydialkylsilyl)-2-butene, 1,4-bis(chlorodiethoxysilyl)-2-butene, 1,4-bis(dichloroethoxysilyl)-2-butene, 1,4-bis(chloroethoxyalkylsilyl)-2-butene, 1,4-bis(tripropoxysilyl)-2-butene, 1,4-bis(dipropoxyalkylsilyl)-2-butene, 1,4-bis(propoxydialkylsilyl)-2-butene, 1,4-bis(chlorodipropoxysilyl)-2-butene, 1,4-bis(dichloropropoxysilyl)-2-butene, 1,4-bis(chloropropoxyalkylsilyl)-2-butene, 1,4-bis(tributoxysilyl)-2-butene, 1,4-bis(dibutoxyalkylsilyl)-2-butene, 1,4-bis(butoxydialkylsilyl)-2-butene, 1,4-bis(chlorodibutoxysilyl)-2-butene, 1,4-bis(dichlorobutoxysilyl)-2-butene, 1,4-bis(chlorobutoxyalkylsilyl)-2-butene, and the fluoro, bromo, iodo and mixed halo analogs, the $C_5$-$C_{20}$ alkoxy analogs, the mixed alkoxy analogs such as 1,4-bis(methoxydiethoxysilyl)-2-butene, and the $C_5$-$C_{20}$ alkene analogs thereof.

Many of these compounds are commercially available. They can also be synthesized using a variety of techniques such as described in U.S. Pat. No. 3,857,825, which is hereby incorporated by reference. Alternatively, these compounds can be prepared by a unique process of the present invention as described hereinafter.

In one or more embodiments, the acyclic multi-functional alkene may be prepared via one or more metathesis reactions. Within these embodiments, the acyclic multifunctional alkene may be prepared by reacting at least two functionalized alpha olefin molecules in the presence of a metathesis catalyst. In one or more embodiments, the alpha olefins may be combined with a ruthenium-based or osmium-based metathesis catalyst such as those described above. In other embodiments, other metathesis catalysts may advantageously be used. In one or more embodiments, a metathesis catalyst that is unaffected or only immaterially affected by the presence of the functional groups present on the alkene is employed. While various metathesis catalysts may be employed, it has advantageously been found that the ruthenium-based or osmium-based catalysts provide technologically useful synthesis with a wide variety of functional groups.

Functional alpha olefins include compounds represented by the formula

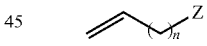

where Z includes a functional group as described above and n includes an integer from 0 to about 20. A mixture of two or more functionalized alpha olefins may be used.

Examples of functional alpha olefins having an Si-containing functional group include allyltrichlorosilane, allyltrimethoxysilane, allyltriethoxysilane, allyltripropoxysilane, allyltributoxysilane, allylchlorodimethoxysilane, allylchlorodiethoxysilane, allylchlorodipropoxysilane, allylchlorodibutoxysilane, allyldichloromethoxysilane, allyldichloroethoxysilane, allyldichloropropoxysilane, allyldichlorobutoxysilane, allylchlorodimethoxysilane, allylchlorodiethoxysilane, allylchlorodipropoxysilane, allylchlorodibutoxysilane, allyldimethylchlorosilane, allyldimethoxysilane, allyldichlorosilane, allyl(chloropropyl)dichlorosilane, allylphenyldichlorosilane, allylmethyldichlorosilane, vinyltrichlorosilane, vinyltrimethoxysilane, vinyltriethoxysilane, vinyltripropoxysilane, vinyltributoxysilane, vinylchlorodimethoxysilane, vinylchlorodiethoxysilane, vinylchlorodipropoxysilane, vinylchlorodibutoxysilane, vinyldichloromethoxysilane, vinyldichloroethoxysilane, vinyldichloropropoxysilane, vinyldichlorobutoxysilane, vinylchlorodimethoxysilane, vinylchlorodiethoxysilane, vinylchlorodipropoxysilane, vinylchlorodibutoxysilane, vinyldimethylchlorosilane, vinyldimethoxysilane, vinyldichlorosilane, vinyl(chloropropyl)dichlorosilane, vinylphenyldichlorosilane, vinylmethyldichlorosilane, 3-butenyldichloromethylsilane, 3-butenyltriethoxysilane, 5-hexenyldimethylchlorosilane, 5-hexenyltrichlorosilane, 5-hexenyltrimethoxysilane, 7-octenyltrichlorosilane, 7-octenyltrimethoxysilane, 7-octenyldimethylchlorosilane, 7-octenyldimethylmethoxysilane, and 7-octenyldimethylethoxysilane.

Examples of functional alpha olefins having an Sn-containing functional group include allyltributyltin, allyltriphenyltin, allyltrimethyltin, allyltrichlorotin, allyltribromotin, tributyl(vinyl)tin, trimethyl(vinyl)tin, triphenyl(vinyl) tin, trichloro(vinyl)tin, tribromo(vinyl)tin, acryloxytriphenylin, acryloxytributytin, diallyldibromotin, diallyldichlorotin, diallyldibutyltin, diallyldimethyltin, diallyldiphenyltin, divinyldibutyltin, divinyldimethyltin, divinyldiphenyltin, divinyldichlorotin, and divinyldibromotin.

In one or more embodiments of the alkene preparation, the alpha olefin is combined with the metathesis catalyst in an inert atmosphere. In one embodiment, the metathesis catalyst can be supported on an inert solid support. In an alternate embodiment, the catalyst and optionally the alpha olefin are dissolved in a solvent prior to being combined.

Examples of solvents that can be used include organic solvents that are inert under the metathesis conditions. Suitable solvents include aromatic hydrocarbons, chlorinated hydrocarbons, ethers, aliphatic hydrocarbons, alcohols, ketones, or mixtures thereof. Examples of useful solvents include benzene, toluene, p-xylene, methylene chloride, dichloroethane, dichlorobenzene, tetrahydrofuran, chloroform, hexanes, heptane, diethylether, pentane, or mixtures thereof. In one embodiment, the solvent may be purified by degassing with an inert atmosphere. If desired, the solvent may be dried.

Metathesis reactions occur over a wide range of temperatures. In one embodiment, the alkene preparation occurs at a temperature of from minus (−) 40° C. to about (+) 100° C., in another embodiment, the temperature is from about minus 20° C. to about 75° C., in yet another embodiment, the temperature is from about 0° C. to about 55° C.

The amount of catalyst employed in the alkene preparation is not critical, however a catalytic amount of catalyst is typically employed. In one embodiment, the amount of catalyst is at least about 0.001 moles catalyst per 100 moles functionalized α-olefin, in other embodiments from about 0.005 to about 10 moles catalyst per 100 moles functionalized α-olefin, and still other embodiments from about 0.01 to about 1 moles catalyst per 100 moles functional α-olefin, and yet another embodiment, about 0.02 to about 0.5 moles catalyst per 100 moles functional α-olefin, is employed.

The order in which the reactants are combined is not particularly limited. In one embodiment, the olefin and functionalizing agent are combined to form a mixture, and then the catalyst is added to the mixture.

The progress of the reaction can be monitored by standard techniques, e.g. gas chromatography, liquid chromatography, HPLC, and nuclear magnetic resonance spectroscopy. In one embodiment, the reaction is terminated by adding a catalyst deactivator. Catalyst deactivators include substances that irreversibly react with the catalyst, such as ethyl vinyl ether.

Conventional procedures such as distillation may be employed to isolate the multifunctional alkene from the solvent after reaction. The alkene may be kept under inert atmosphere to prevent crosslinking or curing.

The acyclic multifunctional alkene can be reacted with one or more metathesis-active olefins (e.g. cycloolefins) in the presence of a metathesis catalyst to form a multi-functional polymer. These reactions may be referred to as ROMP (ring-opening metathesis polymerization), however this label should not be construed to limit this step to only ROMP reactions. In one embodiment, an acyclic olefin can be used along with or in place of the one or more metathesis-active olefins (e.g. cycloolefins). In one embodiment, the reactants and catalysts are preferably contacted in an inert atmosphere. The order of reactant or catalyst addition is not particularly limited. In one embodiment, the acyclic multifunctional alkene and one or more metathesis-active olefins are combined to form a mixture, and then the ruthenium-based or osmium-based catalyst is added to the mixture. One or more of the materials may be introduced together with a solvent. Useful solvents include those described above for use in the alkene preparation.

ROMP reactions typically occur at temperatures that are below the ceiling temperature of the one or more cycloolefins. The ceiling temperature is the temperature above which, due to enthalpy and entropy, ring opening polymerization does not occur to an appreciable extent. In one embodiment, the ROMP step occurs at a temperature of from minus 40° C. to about 100° C., in another embodiment, the temperature is from about minus 20° C. to about 75° C., in yet another embodiment, the temperature is from about 0° C. to about 55° C.

The progress of the reaction can optionally be monitored by standard techniques, as for the alkene preparation, or by monitoring the percent solids. The ROMP reaction may optionally be terminated by adding a catalyst deactivator, such as ethyl vinyl ether.

After reaction, the multi-functional polymer may be isolated from the solvent using conventional procedures. In one or more embodiments, especially where the functional groups are sensitive to water, known techniques can be used to prevent or diminish contact with water. Those of skill in the art will appreciate that exposure of the multi-functional polymer to moisture could result in premature curing.

The amount of acyclic multifunctional alkene and cycloolefin that are employed in the ROMP reaction are not particularly limited. Advantageously, the molar ratio of the acyclic multifunctional alkene to the cycloolefin monomer can be selected to adjust the molecular weight of the polymer. For example, a molecular weight of about 1,000 g/mol to about 100,000 g/mol can be obtained when the molar ratio of acyclic multifunctional alkene to the cycloolefin monomer is from about 1:9 to about 1:1500.

Where a mixture of cycloolefins is employed, the relative amount of each cycloolefin is not particularly limited. In one embodiment, the ratio of first olefin to second olefin is from about 99:1 to about 1:99, in another embodiment, the ratio of first olefin to second olefin is from about 95:5 to about 5:95, in yet another embodiment, the ratio of first olefin to second olefin is from about 90:10 to about 10:90.

The amount of metathesis catalysts (e.g., ruthenium-based or osmium-based catalyst) employed in the ROMP reaction is not critical, however a catalytic amount of catalyst is typically employed. In one embodiment, the amount of catalyst is at least about 0.0001 moles catalyst per 100 moles olefin, in other embodiments at least about 0.001 moles catalyst per 100 moles olefin, in other embodiments, the amount of catalyst is from about 0.005 to about 10 moles catalyst per 100 moles olefin, and still other embodiments from about 0.01 to about 1 moles catalyst per 100 moles olefin, and yet another embodiment about 0.02 to about 0.5 moles catalyst per 100 moles olefin. In these or other embodiments, the mole ratio of catalyst to olefin that is used can be at least about 1:500,000, in other embodiments at least 1:100,000, and in other embodiments at least 1:10,000. In one or more embodiments, the mole ratio of catalyst to olefin is at less than 1:0.5, in other embodiments less than 1:2, and in other embodiments less than 1:100.

In one or more embodiments, the process for making the multi-functional polymer may be conducted in the absence of (or in the limited presence of) a Lewis acid. Lewis acids include, for example, alkyl aluminum halides. In one embodiment, where the acyclic multifunctional alkene includes an alkoxysilane or siloxane group, the amount of Lewis acid present during the ROMP reaction may be limited to less than about 1 mole Lewis acid per mole of alkoxysilane or siloxane. In another embodiment, the amount of Lewis acid present during the ROMP reaction may be less than about 0.5 mole Lewis acid per mole of alkoxysilane or siloxane, even in yet another embodiment, the amount of Lewis acid may be less than about 0.2 mole Lewis acid per mole of alkoxysilane or siloxane. More generally, the amount of Lewis acid present may be based upon the amount of Si, and thus in one embodiment, the amount of Lewis acid present may be less than about 1 mole Lewis acid per mole of Si, in another embodiment, the amount of Lewis acid may be less than about 0.5 mole Lewis acid per mole of Si, in yet another embodiment, the amount of Lewis acid may be less than about 0.2 mole Lewis acid per mole of Si. In still another embodiment, the process of the present invention may be devoid of Lewis acid. The presence of an acid group may cause premature curing in sealant applications under certain conditions, and therefore in certain embodiments, the amount of acid groups is limited.

In one or more embodiments, the polymer produced by the method of this invention can advantageously have a high-trans configuration (i.e., microstructure) and includes multiple functional groups. In one or more embodiments, the trans content of the polymer chain may be at least about 40 percent, in other embodiments at least about 60 percent, and in other embodiments at least about 65 percent of the units of the polymer chain. In one or more embodiments, from about 70 to about 95 percent of the units are in the trans configuration. Advantageously, by employing a mixture of monomers and selecting the comonomer ratio, it is possible to vary the structure and properties of the resulting polymer.

In one or more embodiments, the resulting polymer product advantageously includes a substantial amount of polymer chains having at least one functional end-group (Z). In certain embodiments, the average number of Z groups per polymer molecule can be expressed as the degree of functionality (F). In one embodiment, the multi-functional polymer includes a degree of functionality (F) of at least about 1.2, in other embodiments at least about 1.6, in yet other embodiments at least about 1.8, and in yet other embodiments at least about 1.9. In one embodiment, at least about 80 percent of the polymer molecules contain two or more functional groups, in another embodiment, at least about 90 percent, and in yet another embodiment, at least about 95 percent of the polymer molecules contain two or more functional groups.

In one or more embodiments, the multi-functional polymer includes polymers that can be represented by the formula ZZ where each Z independently includes a functional group as described above, and  includes a high-trans polymer chain. Examples of multi-functional polymer include those represented by the formula $X_a(R)_{3-a}Q$$Q(R)_{3-a}X_a$ where each Q includes Si or Sn, and each X, R, , and a are as described above.

In one embodiment, the Tg of the multi-functional polymer may be less than about 0° C., in other embodiments less than about minus 10° C., and in yet other embodiments less than about minus 15° C. In still another embodiment, the Tg may be from about minus 15 to about minus 115° C.

In one embodiment, the melting point of the multi-functional polymer may be from about minus (−) 40° C. to about (+) 50° C., in other embodiments from about minus 35° C. to about 40° C., and in yet other embodiments from about minus 30° C. to about 20° C.

In certain embodiments, where the polymer backbone is synthesized from two or more different cyclic olefins, the melting point of the multi-functional polymer can be controlled by selecting the relative amounts of cyclic olefins. For example, the melting point of a copolymer prepared from cyclooctadiene and cyclopentene may vary from about minus (−) 30° C. to about (+) 40° C. as the mole fraction of pentene units in the copolymer decrease from about 0.3 to about zero percent, based upon the total moles of cyclooctadiene and cyclopentene.

In one embodiment, the number average molecular weight (Mn) of the polymer is from about 5,000 to about 200,000 g/mol, in other embodiments from about 10,000 to about 175,000 g/mol, and in yet other embodiments from about 15,000 to about 150,000 g/mol, by using standard GPC techniques with polystyrene standards.

In one embodiment, the Brookfield viscosity of the multi-functional polymer, as determined using an 80% solution in xylene at 23° C., may be from about 50 poise (Ps) to about 2,000 Ps, and in another embodiments from about 150 Ps to about 750 Ps.

In certain embodiments, the multifunctional polymer of the present invention is moisture curable and can be cured at atmospheric pressure and room temperature. In certain of these embodiments, the multifunctional polymer includes two or more functional groups that include a crosslinkable moiety as described hereinabove.

In one or more embodiments, the multi-functional polymers are useful in sealant compositions. In addition to the multifunctional polymer, the sealant compositions may include a processing aid, additional polymer, oil, silanol condensation catalysts, fillers, plasticizers, dehydrating agents, co-solubilizers, adhesion improving agents, physical characteristic modifiers, storage stability improving agents, aging inhibitors, ultraviolet absorbers, sequestrants, ozone degradation inhibitors, light stabilizers, amine series radical chain terminators, phosphorus series peroxide decomposers, lubricants, pigments, blowing agents, flame retardants, antistatic agents, and silane compounds.

In other embodiments, the multi-functional polymer may be employed in rubber compositions or vulcanizates, particularly those useful in preparing tire components. When the multi-functional polymer is employed in these applications, the functional end groups may comprise filler-interactive groups, i.e. Z comprises a functional group that will react or interact with carbon black, silica, or both.

The interaction of Z with the filler may occur via chemical reaction, resulting in an ionic or covalent bond between the functional group and the filler particle. Alternately, the interaction of Z with the filler may occur via through-space interaction (e.g. hydrogen bonding, van der Waals interaction, etc.). The interaction may be an attraction that creates a domain within the rubber matrix of the polymer. The interaction may be an affinity toward filler particles that is activated after processing of a vulcanized rubber formulation, e.g. during cure.

In addition to the multi-functional polymer, other ingredients that may be employed in the tire formulations include one or more additional vulcanizable polymers, which may be referred to as rubbers elastomers, fillers, curatives, accelerators, oils, waxes, scorch inhibiting agents, processing aids, zinc oxide, tackifying resins, reinforcing resins, fatty acids such as stearic acid, and peptizers.

Rubbery elastomers that may be used include natural and synthetic elastomers. The synthetic elastomers typically derive from the polymerization of conjugated diene monomers. These conjugated diene monomers may be copolymerized with other monomers such as vinyl aromatic monomers. Other rubbery elastomers may derive from the polymerization of ethylene together with one or more α-olefins and optionally one or more diene monomers.

Useful rubbery elastomers include natural rubber, synthetic polyisoprene, polybutadiene, polyisobutylene-co-isoprene, neoprene, poly(ethylene-co-propylene), poly(styrene-co-butadiene), poly(styrene-co-isoprene), and poly(styrene-co-isoprene-co-butadiene), poly(isoprene-co-butadiene), poly(ethylene-co-propylene-co-diene), polysulfide rubber, acrylic rubber, urethane rubber, silicone rubber, epichlorohydrin rubber, and mixtures thereof. These elastomers can have a myriad of macromolecular structures including linear, branched and star shaped. Other ingredients that are typically employed in rubber compounding may also be added.

Inorganic and organic fillers may be used. The organic fillers include carbon black and starch. The inorganic fillers may include silica, aluminum hydroxide, magnesium hydroxide, clays (hydrated aluminum silicates), and mixtures thereof.

A multitude of rubber curing agents may be employed, including sulfur or peroxide-based curing systems. Curing agents are described in 20 *Kirk-Othmer, Encyclopedia of Chemical Technology*, 365-468, (3$^{rd}$ Ed. 1982), particularly *Vulcanization Agents and Auxiliary Materials*, 390-402, and A. Y. Coran, *Vulcanization* in *Encyclopedia of Polymer Science and Engineering*, (2$^{nd}$ Ed. 1989), which are incorporated herein by reference. Vulcanizing agents may be used alone or in combination.

These rubber formulations are useful for forming tire components such as treads, subtreads, black sidewalls, body ply skins, bead filler, and the like. In one embodiment the multifunctional polymers are employed in tread formulations, and these tread formulations include from about 10 to about 100% by weight, in other embodiments from about 35 to about 90% by weight, and in other embodiments from about 50 to 80% by weight of the multi-functional polymer based on the total weight of the rubber within the formulation.

The preparation of vulcanizable compositions and the construction and curing of the tire is not affected by the practice of this invention. In one embodiment, the vulcanizable rubber composition is prepared by forming an initial masterbatch that includes the rubber component, optionally the multi-functional polymer, and filler. This initial masterbatch is mixed at a starting temperature of from about 25° C. to about 125° C. with a discharge temperature of about 135° C. to about 180° C. To prevent premature vulcanization (also known as scorch), this initial masterbatch generally excludes any vulcanizing agents. Once the initial masterbatch is processed, the vulcanizing agents are introduced and blended into the initial masterbatch at low temperatures in a final mix stage, which does not initiate the vulcanization process. Optionally, additional mixing stages, sometimes called remills, can be employed between the masterbatch mix stage and the final mix stage. The multi-functional polymer may be added at any point up to and including the final mix stage.

Rubber compounding techniques and the additives employed therein are generally known as disclosed in Stephens, *The Compounding and Vulcanization of Rubber*, in *Rubber Technology* (2$^{nd}$ Ed. 1973). The mixing conditions and procedures applicable to silica-filled tire formulations are also well known as described in U.S. Pat. Nos. 5,227,425, 5,719,207, 5,717,022, and European Patent No. 890,606, all of which are incorporated herein by reference.

Where the vulcanizable rubber compositions are employed in the manufacture of tires, these compositions can be processed into tire components according to ordinary tire manufacturing techniques including standard rubber shaping, molding and curing techniques. Typically, vulcanization is effected by heating the vulcanizable composition in a mold; e.g., it is heated to about 140 to about 180° C. Cured or crosslinked rubber compositions may be referred to as vulcanizates, which generally contain three-dimensional polymeric networks that are thermoset. The other ingredients, such as processing aides and fillers, are generally evenly dispersed throughout the vulcanized network. Pneumatic tires can be made as discussed in U.S. Pat. Nos. 5,866,171, 5,876,527, 5,931,211, and 5,971,046, which are incorporated herein by reference.

In yet other embodiments, the multifunctional polymer of this invention may be used to prepare multi-branched polymers. Multi-branched polymers may be prepared by reacting living polymer and a multifunctional polymer bearing functional groups that can react with a living polymer. The living terminus of the living polymer may react via an addition or substitution reaction with a functional group of the multifunctional polymer to form the multi-branched polymer.

In one or more embodiments, the multifunctional polymer includes at least two functional groups that are each capable of reacting with a living polymer to form a bond between the living polymer and the multifunctional polymer.

In one or more embodiments, the functional groups capable of reacting with living polymer include Z-containing groups, where Z is carbon (C), silicon (Si), tin (Sn), germanium (Ge), or lead (Pb). Z-containing functional groups include groups represented by the formula

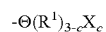

where Θ includes C, Si, Sn, Ge, or Pb, each $R^1$ independently includes hydrogen or a monovalent organic group, each X independently includes a leaving group or addition group, and c includes an integer from 2 to 3. Leaving groups include those substituents that can be displaced by a nucleophilic compound, such as a living polymer anion. In one or more embodiments, the leaving group may react or associate with the living polymer's counter cation (e.g., Li$^+$) and form a stable or neutral compound. Inasmuch as X includes a leaving group, X itself may be a leaving group that is directly attached to Θ and that can be displaced by a nucleophile (e.g., a hydroxy or alkoxy group attached directly to a silicon atom). Or, X may include one or more leaving groups that are displaced by a nucleophile, yet a portion or substituent of the leaving group X is not displaced (e.g., a chlorine atom leaving an acyl chloride group). In certain embodiments, especially where Θ is silicon, the leaving groups may include halogen, alkoxy, and amine groups. In other embodiments, where Θ is carbon, the leaving groups may include acid halide and acid anhydride groups. In one or more embodiments, each X may include multiple leaving groups. For example, each X may include —SiCl3, where each chlorine atom is a leaving group. In one or more embodiments, addition groups include those substituents that will undergo an addition reaction with a nucleophilic compound. In one or more embodiments, the addition group will react or associate with the living anionic portion (e.g., —C⁻) of a living polymer. In one or more embodiments, addition groups include nitriles such as cyano groups, alkyl or alkenyl nitrites, Schiff bases (e.g., RR'C=NR"), ketone groups, aldehyde groups, or ester groups.

In one or more embodiments, the multifunctional polymer includes polymers that can be represented by the formula

where ∿∿ includes a polymer chain, and each $\Theta$, $R^1$, $X$, and $c$ are as described above. Each $\Theta$-containing functional group may react with one or more anionically polymerized living polymer chains.

As with the previous embodiments, the multifunctional polymer can be prepared by combining or reacting olefin and a multifunctional alkene (e.g. functionalizing agent) in the presence of a metathesis catalyst.

In one or more embodiments, the functionalizing agent may include an acyclic functional alkene that includes at least one metathesis-active double bond. In one embodiment, the acyclic functional alkene includes a multifunctional alkene that includes at least one metathesis-active double bond and at least two functional end-groups, which may be the same or different. The acyclic multifunctional alkene includes compounds that can be represented by the formula

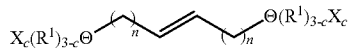

where each $\Theta$, $R^1$, $X$, and $c$ are as described above, and each $n$ is an integer from 0 to about 20.

In one embodiment, where $\Theta$ comprises silicon, the acyclic multifunctional alkene can be represented by the formula

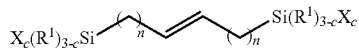

where each $R^1$, $X$, $c$, and $n$ are as described above.

Examples of acyclic multifunctional alkenes include functionalized alpha olefins and $\alpha,\omega$-functionalized olefins. Multifunctional alkenes include bissilyl olefins, bisalkoxysilyl olefins, and bishalosilyl olefins, tin analogs such as bishalostannyl olefins, bisalkoxystannyl olefins, and bisstannyl olefins, as well as germanium and lead analogs.

One specific example includes 1,4-bis(trichlorosilyl)-2-butene. Many of these multifunctional alkenes are commercially available. They can also be synthesized using a variety of techniques, some of which are described in U.S. Pat. No. 3,857,825, which is hereby incorporated by reference. Alternatively, these compounds can be prepared by combining an alpha olefin with a metathesis catalyst as described above.

It will be recognized by one of skill in the art that, when a functional alkene containing just one functional group is employed, a mixture of functionalized polymer molecules, (some including one end-functional group and others including two or more end-functional groups) may be obtained.

In certain embodiments, the multi-functional polymer may be prepared by combining an olefin and a metathesis catalyst, and then the linear polymer may be end-functionalized according to methods known in the art.

Living polymers include those formed by reacting anionic initiators with certain unsaturated monomers to propagate a polymeric segment having a living or reactive end; these polymers may also be referred to as anionically-polymerized living polymers. Anionic polymerization is further described in George Odian, *Principles of Polymerization*, ch. 5 (3$^{rd}$ Ed. 1991), or Panek 94 J. Am. Chem. Soc., 8768 (1972), which are incorporated herein by reference.

Monomers that can be employed in preparing living polymers include any monomer capable of being polymerized according to anionic polymerization techniques. These monomers include those that lead to the formation of elastomeric homopolymers or copolymers. Suitable monomers include, without limitation, conjugated $C_4$-$C_{12}$ dienes, $C_8$-$C_{18}$ monovinyl aromatic monomers, $C_6$-$C_{20}$ trienes, lactones, lactams, and cyclic siloxanes. Examples of conjugated diene monomers include, without limitation, 1,3-butadiene, isoprene, 1,3-pentadiene, 2,3-dimethyl-1,3-butadiene, and 1,3-hexadiene. A non-limiting example of trienes includes myrcene. Aromatic vinyl monomers include, without limitation, styrene, $\alpha$-methyl styrene, p-methylstyrene, vinylnaphthalene, and vinyl pyridine. When preparing elastomeric copolymers, such as those containing conjugated diene monomers and aromatic vinyl monomers, the conjugated diene monomers and aromatic vinyl monomers are normally used at a ratio of 95:5 to 50:50, and in one embodiment at a ratio of 95:5 to 65:35.

In one embodiment, where the living polymer is a copolymer of styrene and 1,3-butadiene (SBR), the styrene content of the SBR copolymer is from about 10 to about 50 percent by weight of the total polymer. In another embodiment the styrene content of the SBR copolymer is from about 18 to about 40 percent by weight of the total polymer. In one embodiment from about 8 to about 99 percent of the units derived from the 1,3-butadiene are of the 1,2-vinyl microstructure, in another embodiment from about 10 to about 60 percent of the units derived from the 1,3-butadiene are of the 1,2-vinyl microstructure. In one embodiment the remaining units derived from the 1,3-butadiene are in the 1,4-cis- or 1,4-trans-microstructure, at a relative ratio of about 3 cis-units to 5 trans-units.

Any anionic initiator can be employed to initiate the formation and propagation of the living polymers. In one embodiment, the anionic initiator comprises at least one element from Group 1 or Group 2 of the Periodic Table, according to the new notation of the IUPAC, as reported in *Hawley's Condensed Chemical Dictionary*, (13$^{th}$ Ed. 1997). The elements in Groups 1 and 2 are commonly referred to as alkali metals and alkaline earth metals, respectively.

Exemplary anionic initiators include, but are not limited to, alkyl lithium initiators such as n-butyl lithium, arenyllithium initiators, arenylsodium initiators, N-lithium dihydro carbon amides, aminoalkyllithiums, and alkyl tin lithiums. Other useful initiators include N-lithiohexamethyleneimide, N-lithiopyrrolidinide, and N-lithiododecamethyleneimide as well as organolithium compounds such as the alkyl lithium adducts of substituted aldimines and substituted ketimines, N-lithio salts of substituted secondary amines, and organosulfur compounds. Exemplary initiators are also described in the following U.S. Pat. Nos. 5,332,810, 5,329,005, 5,578,542, 5,393,721, 5,698,646, 5,491,230, 5,521,309, 5,496,940, 5,574,109, and 5,786,441, which are incorporated herein by reference.

The amount of initiator employed in conducting anionic polymerizations can vary widely based upon the desired polymer characteristics. In one embodiment, the amount of initiator employed is from about 0.1 to about 100, and in another embodiment the amount employed is from about 0.33 to about 10 mmol of initiator per 100 g of monomer.

Anionic polymerizations are typically conducted in a polar solvent such as tetrahydrofuran (THF) or a non-polar hydrocarbon such as the various cyclic and acyclic hexanes, heptanes, octanes, pentanes, their alkylated derivatives, and mixtures thereof, as well as benzene.

A polar coordinator may be added to the polymerization ingredients in order to promote randomization in copolymerization and to control vinyl content. Amounts range between 0 and 90 or more equivalents per equivalent of lithium. The amount depends on the amount of vinyl desired, the level of styrene employed and the temperature of the polymerization, as well as the nature of the specific polar coordinator (modifier) employed.

Compounds useful as polar coordinators include those having an oxygen or nitrogen heteroatom and a non-bonded pair of electrons. Examples include dialkyl ethers of mono and oligo alkylene glycols; "crown" ethers; tertiary amines such as tetramethylethylene diamine (TMEDA); linear THF oligomers; and the like. Specific examples of compounds useful as polar coordinators include tetrahydrofuran (THF), linear and cyclic oligomeric oxolanyl alkanes such as 2,2-bis(2'-tetrahydrofuryl)propane, di-piperidyl ethane, dipiperidyl methane, hexamethylphosphoramide, N—N'-dimethylpiperazine, diazabicyclooctane, dimethyl ether, diethyl ether, tributylamine and the like. The linear and cyclic oligomeric oxolanyl alkane modifiers are described in U.S. Pat. No. 4,429,091, incorporated herein by reference.

Anionically polymerized living polymers can be prepared by either batch or continuous methods. A continuous polymerization is typically begun by charging monomer(s), initiator and solvent at the same time to a suitable reaction vessel. Thereafter, a continuous procedure may be followed that removes product after a suitable residence time and replenishes the reactants. A batch polymerization is generally begun by charging a blend of monomer(s) and normal alkane solvent to a suitable reaction vessel, followed by the addition of the polar coordinator (if employed) and an initiator compound. The reactants may be heated to a temperature of from about 20 to about 200° C. and the polymerization allowed to proceed for from about 0.1 to about 24 hours. This reaction produces a reactive polymer having a reactive or living end. In one embodiment at least about 30 percent of the polymer molecules contain a living end. In another embodiment at least about 50 percent of the polymer molecules contain a living end.

The multi-functional polymer and living polymer may be combined within a solvent, which may optionally be contained under an inert atmosphere. Solvents that are useful include those that were employed to synthesize or store the multifunctional polymer or the living polymer. For example, where the multi-functional polymer is prepared by reacting functional alpha-olefin in the presence of a metathesis catalyst, the isolated polymer may be kept under inert atmosphere to prevent crosslinking or curing, prior to combination with the anionically polymerized living polymer. Alternatively, anionically polymerized living polymer may be added directly to the deactivated reaction mixture of the multifunctional polymer.

The order in which the living polymer and multifunctional polymer are combined is not particularly limited. The polymers are typically combined in an inert atmosphere. In one embodiment, the reaction temperature is less than 150° C., and in another embodiment the temperature is less than 130° C.

In addition to the multifunctional polymer and anionically polymerized living polymer, other components may optionally be added. Optional ingredients include polar coordinators, such as those described above for use in anionic polymerization.

Among the many advantages of one or more embodiments of this invention is the ability to synthesize a wide variety of branched polymers where the backbone and the branches or arms can have a variety of properties. This in part derives from the fact that the backbone and arms are synthesized by employing different synthetic techniques. Moreover, each synthetic technique offers the ability to tailor the resulting polymer, which provides the ability to create a whole host of branched polymers. As known in the art, anionic polymerization techniques allow for the synthesis of polymers having a wide variety of compositional characteristics with a microstructure that can be tailored. Likewise, the characteristics of the backbone, which is formed by metathesis polymerization, can likewise be tailored in characteristics such as, but limited to, melting temperature and glass transition temperature. In one or more embodiments, this provides the ability to create branched polymers where the backbone and arms have one or more similar properties, which may allow them to be miscible with one another. Or, in one or more embodiments, may allow for the production of branched polymers where one or more of the properties of the backbone and arms are dissimilar, which may allow for phase separation of the backbone and arms.

In one or more embodiments, the branched polymers resulting from the foregoing reaction are characterized by including a backbone and at least two branch points, with each branch point extending to at least two branches or arms. In one or more embodiments, each branch point extends to at least three arms, and in other embodiments each branch points extends to at least four arms.

In one or more embodiments, the backbone and the arms are distinct. The difference between the backbone and the arms may include differences in composition, microstructure, or one or more characteristics such as chain length, amount of unsaturation, glass transition temperature, or melting temperature.

In one or more embodiments, the backbone derives from the multifunctional polymer and the branches or arms derive from the living polymer. The location of the functional groups on the multifunctional polymer generally corresponds to the branching points of the branched polymer. Potentially, each functional group of the multifunctional polymer may react with one or more anionically polymerized polymer chains to form one or more branches. Advantageously, "pom-pom" type branched polymer molecules can be prepared by selecting a multifunctional polymer having functional end-groups, where each functional end-group reacts with anionically polymerized polymer to form two or more branches.

In certain embodiments, the polymer backbone of the branched polymer is linear and high-trans. In one embodiment, at least about 40 percent of the units of the polymer backbone are in the trans configuration. In another embodiment, at least about 60 percent, in other embodiments at least 65 percent, in other embodiments at least 80, and in other embodiments at least 85 percent of the units of the polymer backbone are in the trans configuration.

In one or more embodiments, the backbone can be characterized by a molecular weight of from about 0.25 to about 200 times the entanglement molecular weight of the backbone, in another embodiment from about 0.5 to about 150 times the entanglement molecular weight, and in yet another embodiment from about 1 to about 100 times the entanglement molecular weight of the backbone. In certain embodiments, especially where the multi-branched polymer is used in the manufacture of tires, the backbone can be characterized by a molecular weight of from about 30 to about 60 times the entanglement molecular weight of the backbone. In certain embodiments, especially where the multi-branched polymer is used in adhesive compositions, the backbone can be characterized by a molecular weight of from about 5 to about 30 times the entanglement molecular weight of the backbone. The entanglement weight or length of a polymer chain refers to a number of polymer chain repeating (or mer) units that correspond to a molecular weight sufficiently large for entanglements to occur between molecules of undiluted polymer. This length corresponds to a molecular weight where the slope of a plot of log viscosity vs. log molecular weight changes from about 1.0 to about 3.4; the change being associated with intermolecular entanglements. In general, the entanglement length has been defined as that length of polymer resulting from about 100 mer units. For purposes of this specification, entanglement length refers to a polymer chain length that includes a number of mer units on the order of magnitude of 100. For example, the entanglement length for polystyrene has been experimentally determined to be about 340 mer units, a number that is on the order of magnitude of 100. Additional experimental techniques for determining the entanglement length of a polymer are summarized by W. W. Graessley in ADV. POLYM. SCI., Vol. 16, 1974.

In one or more embodiments, the backbone is characterized by including at least one melt temperature. The melting temperature can vary widely, and can be controlled by factors known in the art. In one embodiment, where the polymer exhibits some crystalline character either quiescent or under strain, the melting point is from about −40° C. to about 120° C., in another embodiment, from about −35° C. to about 100° C., and in yet another embodiment, from about −30° C. to about 80° C. It will be understood by one of skill in the art that, in embodiments where the arms are immiscible with the backbone, multiple melting points may be observed.

In certain embodiments, where the polymer backbone is prepared by using two or more cyclic olefins, the melting point of the multifunctional polymer can be controlled or manipulated by selecting the relative amounts of cyclic olefins. For example, the melting point of a copolymer backbone prepared from cyclooctadiene and cyclopentene may vary from about −30° C. to about 40° C. as the mole fraction of pentenyl repeat units in the copolymer decrease from about 0.3 to about zero percent, based upon the total moles of butenyl and pentenyl repeat units. Advantageously, in one or more embodiments, the glass transition temperature of the backbone can remain relatively constant despite the change in melting temperature.

Because the arms of the multi-branched polymers of this invention derive from anionically polymerized, living polymers, the characteristics thereof can be altered in several respects. In one or more embodiments, the composition of the arms can be varied by the selection of one or more of a multitude of monomers that can be anionically polymerized. Also, by using modifiers, the microstructure of the polymer can be altered. For example, in the case of polymerized units of 1,3-butadiene, the vinyl content of the polymer can be varied from at least 8% to about 99%, which generally alters the cis and trans 1,4 content proportionately.

The arms may also be characterized by a molecular weight from about 0.25 to about 200 times the entanglement molecular weight of the arms, in another embodiment from about 0.5 to about 100 times the entanglement molecular weight, and in yet another embodiment from about 1 to about 10 times the entanglement molecular weight of the arms.

The branch points (i.e. where the polymer backbone is bonded to one or more anionically polymerized polymer branches) can be anywhere along the polymer backbone however, advantageous results are achieved when there is a branch point at or near each end of the polymer backbone.

In certain embodiments, the branched polymer includes polymers that can be represented by the formula

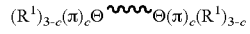

where each $\pi$ independently includes an anionically-polymerized polymer chain, each $\Theta$ independently includes C, Si, Ge, Sn, or Pb, each $R^1$ independently includes hydrogen or a monovalent organic group, each c independently includes an integer from 2 to 3, and ～～ comprises the polymer backbone. This multi-branched polymer may derive from the coupling of foregoing arms to the foregoing backbone, and therefore the characteristics of the arms and backbone may be the same as those described above.

In one or more embodiments, where the arms are miscible with the backbone, one glass transition temperature may typically be observed. Where the arms are not miscible with the backbone, multiple glass transition temperatures may be observed. In one or more embodiments, the multi-branched polymers may include a glass transition temperature ($T_g$) that is less than −5° C., in another embodiment less than −10° C., and in yet another embodiment less than −15° C.

In one embodiment, the branched polymer may be employed in rubber compositions or vulcanizates, particularly those useful in preparing tire components. These tire components can be prepared as described hereinabove. The branched polymers of this invention may be used alone or together with other rubbery elastomers.

These rubber formulations are useful for forming tire components such as treads, subtreads, black sidewalls, body ply skins, bead filler, and the like. In one embodiment the branched polymers are employed in tread formulations, and these tread formulations will include from about 1 to about 100% by weight of the branched polymer based on the total rubber within the formulation. In another embodiment, the tread formulations include from about 5 to about 50% by weight, and in yet another embodiment from about 10 to 30% by weight of the branched polymer based on the total weight of the rubber within the formulation. The preparation of vulcanizable compositions and the construction and curing of the tire is not affected by the practice of this invention.

In order to demonstrate the practice of the present invention, the following examples have been prepared and tested. The examples should not, however, be viewed as limiting the scope of the invention. The claims will serve to define the invention.

EXAMPLES

Example 1

A solution of 25 mL (24.7 g, 0.15 mol) allyl trimethoxysilane in 100 mL dry, distilled methylene chloride was prepared in an oven-dried 200 mL Schlenk flask fitted with a condenser. A solution of 0.79 g ($9.3 \times 10^{-4}$ mol) Grubbs 2nd generation ruthenium catalyst in 10 mL dry toluene was added via cannula to the olefin. Under a nitrogen purge, the resulting mixture was heated to 50° C. for about 16 hours. The product alkene was isolated by multi-step distillation. Excess solvent was removed by heating the resultant mixture to 140° C. under an inert atmosphere. The clear, colorless liquid product was distilled at 86-90° C. under 1.5 mmHg reduced pressure. Approximately 13 g (58% yield) of product was recovered. NMR and GC analyses were used. Approximately 34% of the product contained a vinyl silyl group. The trans:cis ratio of the product was approximately 3:1.

Example 2

To a 1 gallon reactor was added 385 mL (297 g, 4.4 mol) dry cyclopentene, 4.4 mL (4.6 g, 0.015 mol) 1,4-bis(trimethoxysilyl)-2-butene and 600 mL (385 g) dry hexanes. The reactor contents were heated to about 100° F. A solution of 40 mg ($4.7 \times 10^{-5}$ mol) Grubbs' $2^{nd}$ generation ruthenium catalyst in 10 mL dry toluene was added to the reactor via injection port, and the contents were stirred for about two hours. Ethyl vinyl ether (5 mL) in 50 mL dry hexanes was added to the reactor. The polymer was removed from the reactor. The solvent was removed under reduced pressure. Gel permeation chromatography (GPC) indicated that the polymer had a Mn of 15,100 g/mol and a Mw/Mn of 1.61. Thermal analysis indicated that the polymer had a Tg of minus 112° C. and a Tm of 14.6° C. NMR analysis indicated that the polymer had a microstructure that was 83.3 percent trans olefin. The polymer cured upon exposure to atmospheric moisture.

Example 3

To a 1 gallon reactor was added 125 mL (109.8 g, 1.0 mol) dry 1,5-cyclooctadiene, 325 mL (250 g, 3.7 mol) dry cyclopentene, 0.3 mL (0.3 g, 0.003 mol) 1,4-bis(trimethoxysilyl)-2-butene and 630 mL dry, degassed toluene. The reactor contents were heated to about 100° F. under 30 psi nitrogen. A solution of 50 mg Grubbs' $2^{nd}$ generation ruthenium catalyst in 10 mL dry toluene was added to the reactor, and the contents were stirred for about two hours, then 5 mL ethyl vinyl ether in 50 mL dry hexanes was added to the reactor. The polymer was removed from the reactor. The solvent was removed under reduced pressure. GPC analysis indicated the polymer had a Mn of 63,900 g/mol and a Mw of 108,400, and NMR analysis indicated 62.3% pentenamer units and 37.7% butadiene units. The polymer cured upon exposure to atmospheric moisture.

Example 4

The backbone of a multi-branched polymer was prepared according to the following ROMP reaction. To a 2 gallon reactor was added 280 milliliters (mL) dry 1,5-cyclooctadiene, 160 mL dry cyclopentene, 0.75 mL 1,4-bis(trichlorosilyl)-2-butene and 682 mL dry, degassed toluene. The reactor contents were stirred and heated to about 100° F. under 30 psi nitrogen. A solution of 35 milligrams (mg) Grubbs' $2^{nd}$ generation ruthenium catalyst in 10 mL toluene was added to the reactor, and the contents were stirred for about one hour. An exothermic peak of about 105° F. was observed. After about 90 minutes 5 mL ether vinyl ether was added to the reactor. Analysis of this ROMP, linear polymer showed a number average molecular weight (Mn) of 46,900, a weight average molecular weight (Mw) of 79,900, and polydispersity index (PDI) of 1.70.

The arms of the multi-branched polymer were prepared as follows. To a 1 gallon reactor was added 617 grams (g) hexane and 1600 g of a 21.7% weight/weight butadiene in hexanes blend. The reactor contents were stirred and heated to about 150° F. When the temperature of the reactor contents reached about 147° F., 20.6 mL of 1.68 M n-butyl lithium in hexanes was added. An exothermic peak of about 222° F. was observed within about 5 minutes, and heated at 150 C for about 2 hours. Analysis of quenched samples of this living polymer showed a $M_n$ of 11,200, a $M_w$ of 12,200, and a PDI of 1.10.

The backbone and arms were combined to form the multi-branched polymer by coupling the living polymers (i.e. arms) to the ROMP polymer (i.e. backbone). After about 30 minutes, the living polymer cement was transferred to the 2 gallon reactor containing the polymer prepared above, at about 100° F. The reactor contents were stirred, and after about 3 hours, 150 mL of tetrahydrofuran was added. After about 18 hours 4.5 mL of 1.68 M n-butyl lithium in hexanes was added, and the reactor contents were stirred for about 2 hours. The contents of the reactor were cooled to about room temperature and a mixture of isopropanol/BHT was added. The branched polymer was coagulated by using a mixture of 1:8 hexanes:ethyl acetate. About 23.6% of the excess polybutadiene remained unreacted.

Example 5

A linear polymer was prepared according to the following ROMP polymerization. To a 1 gallon reactor was charged 230 mL (177.0 g, 2.6 mol) dry cyclopentene, 415 mL (365.4 g, 3.4 mol) dry 1,5-cyclooctadiene, 0.5 mL (0.4 g, 0.0043 mol) 3-hexene, and 900 mL dry, degassed toluene. The reactor contents were stirred and heated to about 100° F. under 30 psi nitrogen. A solution of 52 milligrams (mg) ($6.1 \times 10^{-5}$ mol) Grubbs' $2^{nd}$ generation ruthenium catalyst in 10 mL dry toluene was added to the reactor, and the contents were stirred for about one hour. An exothermic peak of about 115° F. was observed, and the viscosity increased. After about 180 minutes, 5 mL ether vinyl ether was added to the reactor. The polymer product was analyzed by NMR and GPC instrumentation and showed the following: $M_n$=40,400 g/mol; $M_w$=65,300 g/mol; $M_w/M_n$=1.61; 24.6 mol % pentenamer, 75.4 mol % butadiene units in polymer.

Example 6

Anionically polymerized polymer similar to that employed to form the arms of the branched polymer of Example 4 were prepared as follows. Into nitrogen-purged, dry 750 mL bottles, 97 g hexane and 203 g butadiene blend (22.2% weight/weight butadiene in hexane) were charged. 2.7 mL of 1.68 M N-butyl lithium was added and the bottles were placed in a 50° C. bath for one hour. The bottle contents were cooled and 1 mL isopropanol was added to terminate the reaction.

The linear polymer of Example 5 and the anionically polymerized polymer of this Example were blended as follows. A blend of 50:50 by weight of the linear ROMP polymer and anionically polymerized polymer was prepared by combining the toleuene solution of the linear polymer and the hexane solution of the anionically polymerized polymer and mixing, evaporating the solvents, and drying. No reaction or coupling between the living polymer and the ROMP polymer was believed to occur.

Analysis

Adhesion properties for the foregoing three samples (i.e. Example 4, which was a multi-branched polymer, Example 5, which was a linear ROMP polymer, and Example 6, which was a blend of anionically polymerized polymer and ROMP polymer) were evaluated and results are summarized in Table 1. Specifically, a 0.3 mm thick layer of sample was formed between two 10 mm diameter aluminum plates. At about 25° C., the plates were separated at a rate of 3.0 mm/sec and the time-dependent force was measured. The adhesion energy, or work of adhesion ($W_{adh}$) was determined by multiplying the initial thickness (0.3 mm) by the integration of the engineering stress-strain response that was recorded during debonding.

TABLE I

| Example No. | Description | $W_{adh}$ (J/m²) |
|---|---|---|
| 1 | Multi-branched polymer | 119 |
| 2 | ROMP Linear polymer | 56 |
| 3 | Mixture (ROMP polymer and Anionically-Polymerized polymer) | 33 |

The plot of stress versus strain for Examples 4-6 is shown in FIG. 1. The broad shoulder on the curve for Example 4 (the branched polymer), is typically seen for polymers with macrostructures that engender strain hardening.

Various modifications and alterations that do not depart from the scope and spirit of this invention will become apparent to those skilled in the art. This invention is not to be duly limited to the illustrative embodiments set forth herein.

What is claimed is:

1. A method for preparing a multi-functional polymer, comprising:
reacting at least two functionalized alpha olefin molecules in the presence of a metathesis catalyst thereby forming an alkene comprising multiple functionalities, where the alpha olefin molecules may be the same or different, where the multiple functionalities are selected from methacrylates, acrylates, cinnamates, epoxides, lactones, cyclic carbonates, tetrahydrofurans, oxetanes, lactams, phosphazenes, and groups represented by the formula

where Q comprises Si or Sn, each R independently comprises a hydroxyl, a hydrolyzable group, or a monovalent organic group containing from 1 to about 20 carbon atoms, each X comprises a hydrolyzable group or a hydroxyl group, and a is an integer from 1 to about 3; and
reacting the alkene with a metathesis polymerizable olefin in the presence of a metathesis catalyst thereby forming a multi-functional polymer.

2. The method of claim 1, where the metathesis polymerizable olefin comprises cyclopropene, cyclobutene, benzocyclobutene, cyclopentene, dicyclopentadiene, norbornene, norbornadiene, cycloheptene, cyclooctene, 7-oxanorbornene, 7-oxanobornadiene, cyclodecene, 1,3-cyclooctadiene, 1,5-cyclooctadiene, 1,3-cycloheptadiene, [2.2.1]bicycloheptenes, [2.2.2]bicyclooctenes, cyclohexenylnorbornenes, norbornene dicarboxylic anhydrides, cyclododecene, 1,5,9-cyclododecatriene, or a mixture thereof.

3. A method for preparing a multi-functional polymer, the method comprising the steps of:
reacting two or more alpha olefin molecules represented by the formula

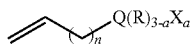

where Q comprises Si or Sn, each R independently comprises a hydroxyl, a hydrolyzable group, or a monovalent organic group containing from 1 to about 20 carbon atoms, each X comprises a hydrolyzable group or a hydroxyl group, a is an integer from 1 to about 3, and n is an integer from 0 to about 20, in the presence of a metathesis catalyst to form an alkene represented by the formula

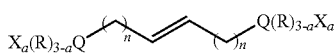

where each Q comprises Si or Sn, each R independently comprises a hydroxyl, a hydrolyzable group, or a monovalent organic group containing from 1 to about 20 carbon atoms, each X comprises a hydrolyzable group or a hydroxyl group, a is an integer from 1 to about 3, and n is an integer from 0 to about 20; and
reacting the alkene with a first metathesis polymerizable olefin and a second metathesis polymerizable olefin, in the presence of a ruthenium-based or osmium-based metathesis catalyst, thereby forming a multi-functional polymer represented by the formula

where each Q comprises Si or Sn, each R independently comprises a hydroxyl, a hydrolyzable group, or a monovalent organic group containing from 1 to about 20 carbon atoms, each X comprises a hydrolyzable group or a hydroxyl group, and a is an integer from 1 to about 3, and ∿∿∿ comprises a polymer chain, and where the ratio of first metathesis polymerizable olefin to second metathesis polymerizable olefin is from about 99:1 to about 1:99.

4. The method of claim 3, where the alpha olefin comprises allyltrichlorosilane, allyltrimethoxysilane, allyltriethoxysilane, allyltripropoxysilane, allyltributoxysilane, allylchlorodimethoxysilane, allylchlorodiethoxysilane, allylchlorodipropoxysilane, allylchlorodibutoxysilane, allyldichloromethoxysilane, allyldichloroethoxysilane, allyldichloropropoxysilane, allyldichlorobutoxysilane, allylchlorodimethoxysilane, allylchlorodiethoxysilane, allylchlorodipropoxysilane, allylchlorodibutoxysilane, allyldimethylchlorosilane, allyldimethoxysilane, allyldichlorosilane, allyl(chloropropyl)dichlorosilane, allylphenyldichlorosilane, allylmethyldichlorosilane, vinyltrichlorosilane, vinyltrimethoxysilane, vinyltriethoxysilane, vinyltripropoxysilane, vinyltributoxysilane, vinylchlorodimethoxysilane, vinylchlorodiethoxysilane, vinylchlorodipropoxysilane, vinylchlorodibutoxysilane, vinyldichloromethoxysilane, vinyldichloroethoxysilane, vinyldichloropropoxysilane, vinyldichlorobutoxysilane, vinylchlorodimethoxysilane, vinylchlorodiethoxysilane, vinylchlorodipropoxysilane, vinylchlorodibutoxysilane, vinyldimethylchlorosilane, vinyldimethoxysilane, vinyldichlorosilane, vinyl(chloropropyl)dichlorosilane, vinylphenyldichlorosilane, vinylmethyldichlorosilane, 3-butenyldichloromethylsilane, 3-butenyltriethoxysilane, 5-hexenyldimethylchlorosilane, 5-hexenyltrichlorosilane, 5-hexenyltrimethoxysilane, 7-octenyltrichlorosilane, 7-octenyltrimethoxysilane, 7-octenyldimethylchlorosilane, 7-octenyldimethylmethoxysilane, and 7-octenyldimethylethoxysilane, allyltributyltin, allytriphenyltin, allyltrimethyltin, allyltrichlorotin, allytribromotin, tributyl(vinyl)tin, trimethyl(vinyl)tin, triphenyl(vinyl)tin, trichloro(vinyl)tin, tribromo(vinyl)tin, acryloxytriphenytin, acryloxytributytin, diallyldibromotin, diallyldichlorotin, diallyldibutyltin, diallyldimethyltin, diallyldiphenyltin, divinyldibutyltin, divinyldimethyltin, divinyldiphenyltin, divinyldichlorotin, divinyldibromotin, or mixtures thereof.

5. The method of claim 3, where the alkene comprises a bis silyl olefin, bis alkoxysilyl olefin, or bis halosilyl olefin.

6. The method of claim 3, where the first metathesis polymerizable olefin and second metathesis polymerizable olefin each independently comprise a compound represented by the formula

where z is an integer from 1 to about 18.

7. The method of claim 3, where the first metathesis polymerizable olefin and second metathesis polymerizable olefin each independently comprise cyclopropene, cyclobutene, benzocyclobutene, cyclopentene, dicyclopentadiene, norbornene, norbornadiene, cycloheptene, cyclooctene, 7-oxanorbornene, 7-oxanorbornadiene, cyclodecene, 1,3-cyclooctadiene, 1,5-cyclooctadiene, 1,3-cycloheptadiene, [2.2.1]bicycloheptenes, [2.2.2]bicyclooctenes, cyclohexenylnorbornenes, norbornene dicarboxylic anhydrides, cyclododecene, or 1,5,9-cyclododecatriene.

8. A method for preparing a moisture-curable polymer, comprising:
reacting (a) a first metathesis polymerizable olefin, (b) a second metathesis polymerizable olefin, where said second metathesis polymerizable olefin differs from said first metathesis polymerizable olefin in ring size or in substituents, or where said second metathesis polymerizable olefin comprises an isomer of said first metathesis polymerizable olefin, and (c) an acyclic alkene comprising at least one double bond and comprising multiple crosslinkable functional groups, in the presence of a ruthenium-based or osmium-based metathesis catalyst thereby forming a moisture-curable polymer, where the ratio of first metathesis polymerizable olefin to second metathesis polymerizable olefin is selected to produce a moisture-curable polymer having a melting point of from about minus 40° C. to about 100° C.

9. The method of claim 8, where the first metathesis polymerizable olefin and second metathesis polymerizable olefin each independently comprise cyclopropene, cyclobutene, benzocyclobutene, cyclopentene, dicyclopentadiene, norbornene, norbornadiene, cycloheptene, cyclooctene, 7-oxanorbornene, 7-oxanorbornadiene, cyclodecene, 1,3-cyclooctadiene, 1,5-cyclooctadiene, 1,3-cycloheptadiene, [2.2.1]bicycloheptenes, [2.2.2]bicyclooctenes, cyclohexenylnorbornenes, norbornene dicarboxylic anhydrides, cyclododecene, or 1,5,9-cyclododecatriene.

10. The method of claim 8, where the crosslinkable functional groups are selected from methacrylates, acrylates, cinnamates, epoxides, lactones, cyclic carbonates, tetrahydrofurans, oxetanes, lactams, phophazenes, and groups represented by the formula $Q(R)_{3-a}X_a$ where Q comprises Si or Sn, each R independently comprises a hydroxyl, a hydrolyzable group, or a monovalent organic group containing from 1 to about 20 carbon atoms, each X comprises a hydrolyzable group or a hydroxyl group, and a is an integer from 1 to about 3.

11. A method for preparing a multi-branched polymer comprising:
preparing a multifunctional polymer by reacting:
an olefin including a metathesis-active double bond and a compound represented by the formula

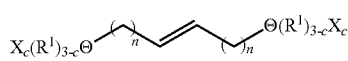

where each Θ independently includes carbon, silicon, germanium, tin, or lead, each $R^1$ independently includes hydrogen or a monovalent organic group, each X independently comprises a leaving group, each c independently includes an integer from 2 to 3, and each n is an integer from 0 to about 20 in the presence of a metathesis catalyst; and combining the multifunctional polymer with living polymer to form the multi-branched polymer.

12. The method of claim 11, where the olefin comprises an acyclic olefin, a cyclic olefin, or a mixture of two or more acyclic or cyclic olefins.

13. The method of claim 11, where Θ comprises Si.

14. A branched polymer represented by the formula

where each π independently includes a polymer chain,  comprises a polymer, each Θ independently includes carbon, silicon, germanium, tin, or lead, each $R^1$ independently includes hydrogen, or a monovalent organic group, and each c independently includes an integer from 2 to 3, where  derives from a metathesis-catalyzed polymerization and each π derives from an anionic polymerization.

15. The trans polymer of claim 14, where each π derives from the polymerization of monomer including 1,3-butadiene.

16. The polymer of claim 14, where π is characterized by a molecular weight of 0.25 to about 200 times the entanglement molecular weight.

17. A multi-functional polymer represented by the formula
ZZ where each Z independently includes a crosslinkable moiety and  is a linear high-trans polymer chain, where at least 40% of the units of the high trans polymer chain are in the trans configuration.

18. The polymer of claim 17, where the crosslinkable moiety is selected from the group consisting of methacrylates, acrylates, cinnamates, epoxides, lactones, cyclic carbonates, tetrahydrofurans, oxetanes, lactams, phosphazenes, and tin- or silicon-containing groups that have a hydroxyl or hydrolyzable group bound to a tin or silicon atom.

19. The polymer of claim 17, where the multi-functional polymer is represented by the formula

where Q includes Si or Sn, and each R independently includes a hydroxyl, a hydrolyzable group, or a monovalent organic group containing from 1 to about 20 carbon atoms, each X includes a hydrolyzable group or a hydroxyl group, and a includes an integer from 1 to about 3.

20. The polymer of claim 19, where the Tg of the multi-functional polymer is less than 0° C.

21. The polymer of claim 20, where the melting point of the multi-functional polymer is from about −40° C. to about +50° C.

22. The polymer of claim 17, where the high trans polymer chain derives from the polymerization of two or more different cyclic olefins.

23. The polymer of claim 21, where the high trans polymer chain derives from the polymerization of cyclooctadiene and cyclopentene.

24. The polymer of claim 17, where the number average molecular weight of the multi-functional polymer is from about 5,000 to about 200,000 g/mol.

25. The polymer of claim 17, where at least 60% of the units of the high trans polymer chain are in the trans configuration.

26. The method of claim 1, where the metathesis catalyst is a ruthenium-based or osmium-based metathesis catalyst.

27. The method of claim 11, where the metathesis catalyst is a ruthenium-based or osmium-based metathesis catalyst.

28. The method of claim 1, where the metathesis catalyst is selected from the group consisting of ruthenium, dichloro(phenylmethylene)bis(tricyclohexylphosphine), ruthenium, [1,3-bis-(2,4,6-trimethylphenyl)-2-imidazolidinylidene]dichloro(phenylmethylene)(tricyclohexylphosphine), ruthenium, dichloro [[2-(1-methylethoxy)phenyl]methylene](tricyclohexylphosphine), and ruthenium, [1,3-bis (2,4,6-trimethylphenyl)-2-imidazolidinylidene]dichloro [[2,(1-methylethoxy)phenyl]methylene].

29. The method of claim 3, where the metathesis catalyst is selected from the group consisting of ruthenium, dichloro(phenylmethylene)bis(tricyclohexylphosphine), ruthenium, [1,3-bis-(2,4,6-trimethylphenyl)-2-imidazolidinylidene]dichloro(phenylmethylene)(tricyclohexylphosphine), ruthenium, dichloro [[2-(1-methylethoxy)phenyl]methylene](tricyclohexylphosphine), and ruthenium, [1,3-bis(2,4,6-trimethylphenyl)-2-imidazolidinylidene]dichloro [[2,(1-methylethoxy)phenyl]methylene].

30. The method of claim 8, where the metathesis catalyst is selected from the group consisting of ruthenium, dichloro(phenylmethylene)bis(tricyclohexylphosphine), ruthenium, [1,3-bis-(2,4,6-trimethylphenyl)-2-imidazolidinylidene]dichloro(phenylmethylene)(tricyclohexylphosphine), ruthenium, dichloro [[2-(1-methylethoxy)phenyl]methylene](tricyclohexylphosphine), and ruthenium, [1,3-bis(2,4,6-trimethylphenyl)-2-imidazolidinylidene]dichloro [[2,(1-methylethoxy)phenyl]methylene].

31. The method of claim 11, where the metathesis catalyst is selected from the group consisting of ruthenium, dichloro(phenylmethylene)bis(tricyclohexylphosphine), ruthenium, [1,3-bis-(2,4,6-trimethylphenyl)-2-imidazolidinylidene]dichloro(phenylmethylene)(tricyclohexylphosphine), ruthenium, dichloro [[2-(1-methylethoxy)phenyl]methylene](tricyclohexylphosphine), and ruthenium, [1,3-bis (2,4,6-trimethylphenyl)-2-imidazolidinylidene]dichloro [[2,(1-methylethoxy)phenyl]methylene].

32. The method of claim 1, where the metathesis catalyst is defined by the formula

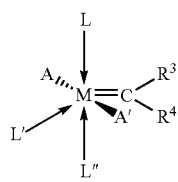

where M includes ruthenium or osmium, L, L', L" each independently include any neutral electron donor ligand, A, A', and A" each independently include an anionic substituent, and $R^3$ and $R^4$ independently comprise hydrogen or an organic group.

33. The method of claim 3, where the metathesis catalyst is defined by the formula

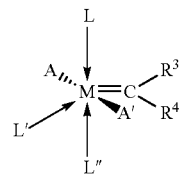

where M includes ruthenium or osmium, L, L', L" each independently include any neutral electron donor ligand, A, A', and A" each independently include an anionic substituent, and $R^3$ and $R^4$ independently comprise hydrogen or an organic group.

34. The method of claim 8, where the metathesis catalyst is defined by the formula

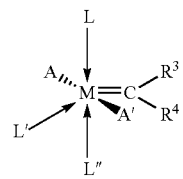

where M includes ruthenium or osmium, L, L', L" each independently include any neutral electron donor ligand, A, A', and A" each independently include an anionic substituent, and $R^3$ and $R^4$ independently comprise hydrogen or an organic group.

35. The method of claim 11, where the metathesis catalyst is defined by the formula

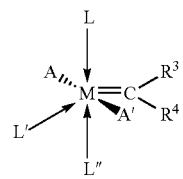

where M includes ruthenium or osmium, L, L', L" each independently include any neutral electron donor ligand, A, A', and A" each independently include an anionic substituent, and $R^3$ and $R^4$ independently comprise hydrogen or an organic group.

36. The method of claim 2, where the metathesis polymerizable olefin is a mixture of 1,5-cyclooctodiene and cyclopentene.

37. The method of claim 7, where the metathesis polymerizable olefin is a mixture of 1,5-cyclooctodiene and cyclopentene.

38. The method of claim 9, where the metathesis polymerizable olefin is a mixture of 1,5-cyclooctodiene and cyclopentene.

39. The method of claim 12, where the metathesis polymerizable olefin is a mixture of 1,5-cyclooctadiene and cyclopentene.

* * * * *